United States Patent
Walker et al.

(10) Patent No.: US 10,058,674 B2
(45) Date of Patent: Aug. 28, 2018

(54) SYSTEMS FOR ENHANCING SLEEP

(71) Applicant: Ebb Therapeutics, Inc., Pittsburgh, PA (US)

(72) Inventors: Rick W. Walker, Stow, OH (US); Edward P. G. Doughertry, Stow, OH (US); Jason A. Belton, Norton, OH (US); Robert E. Tucker, Sanibel, FL (US); Jeffrey J. Schirm, Monroeville, PA (US)

(73) Assignee: Ebb Therapeutics, Inc., Pittsburgh, PA (US)

( * ) Notice: Subject to any disclaimer, the term of this patent is extended or adjusted under 35 U.S.C. 154(b) by 213 days.

(21) Appl. No.: 14/758,438

(22) PCT Filed: Jan. 2, 2014

(86) PCT No.: PCT/US2014/010070
§ 371 (c)(1),
(2) Date: Jun. 29, 2015

(87) PCT Pub. No.: WO2014/107509
PCT Pub. Date: Jul. 10, 2014

(65) Prior Publication Data
US 2015/0352314 A1    Dec. 10, 2015

Related U.S. Application Data

(60) Provisional application No. 61/748,409, filed on Jan. 2, 2013, provisional application No. 61/859,161, filed on Jul. 26, 2013.

(51) Int. Cl.
*A61F 7/10*    (2006.01)
*A61F 7/08*    (2006.01)
(Continued)

(52) U.S. Cl.
CPC ............... *A61M 21/02* (2013.01); *A61F 7/02* (2013.01); *A61F 2007/0007* (2013.01);
(Continued)

(58) Field of Classification Search
CPC ................. A61F 2007/0054; A61F 2007/0056
See application file for complete search history.

(56) References Cited

U.S. PATENT DOCUMENTS 222,690 A    12/1879    Goldschmidt
301,931 A    7/1884    Smith et al.
(Continued)

FOREIGN PATENT DOCUMENTS

EP    1977710    10/2008
EP    2359781    8/2011
(Continued)

OTHER PUBLICATIONS

Nofzinger; U.S. Appl. No. 14/749,590 entitled "Methods, devices and systems for treating insomnia by inducing frontal cerebral hypotherma," filed Jun. 24, 2015.
(Continued)

*Primary Examiner* — Kaitlyn Smith
(74) *Attorney, Agent, or Firm* — Shay Glenn LLP

(57) ABSTRACT

Methods, devices and systems for improving sleep (including reducing sleep onset and maintenance of sleep duration), enhancing, or increasing sleep, including (but not limited to) treating sleeping disorders such as insomnia.

34 Claims, 20 Drawing Sheets

(51) Int. Cl.
*A61M 21/02* (2006.01)
*A61F 7/02* (2006.01)
*A61M 21/00* (2006.01)
*A61F 7/00* (2006.01)

(52) U.S. Cl.
CPC ............. *A61F 2007/0054* (2013.01); *A61F 2007/0072* (2013.01); *A61F 2007/0076* (2013.01); *A61F 2007/0093* (2013.01); *A61M 2021/0066* (2013.01); *A61M 2021/0083* (2013.01); *A61M 2205/3368* (2013.01); *A61M 2205/3389* (2013.01); *A61M 2205/362* (2013.01); *A61M 2205/366* (2013.01); *A61M 2205/3626* (2013.01); *A61M 2205/3633* (2013.01); *A61M 2205/3653* (2013.01); *A61M 2205/3673* (2013.01); *A61M 2205/42* (2013.01); *A61M 2205/502* (2013.01); *A61M 2205/505* (2013.01); *A61M 2205/583* (2013.01); *A61M 2209/088* (2013.01); *A61M 2210/06* (2013.01); *A61M 2210/0693* (2013.01)

(56) References Cited

U.S. PATENT DOCUMENTS

| | | |
|---|---|---|
| 683,991 A | 10/1901 | Rowe |
| 737,473 A | 8/1903 | Porter |
| 805,371 A | 11/1905 | Meinecke et al. |
| 919,614 A | 4/1909 | Meinecke |
| 1,002,021 A | 8/1911 | Barnes |
| 1,127,221 A | 2/1915 | Finkelstein |
| 1,318,411 A | 10/1919 | Rozene |
| 1,322,984 A | 11/1919 | Wesley |
| 1,345,906 A | 7/1920 | Augustine |
| 1,511,775 A | 10/1924 | Frederic et al. |
| 1,522,295 A | 1/1925 | Gee |
| 1,567,931 A | 12/1925 | Epler |
| 1,743,244 A | 1/1930 | Shulman |
| 1,769,186 A | 7/1930 | Morris |
| 1,870,143 A | 8/1932 | Roux |
| 1,964,655 A | 6/1934 | Williamson |
| 2,049,723 A | 8/1936 | Pomeranz |
| 2,158,571 A | 5/1939 | Culp |
| 2,320,467 A | 6/1943 | Rabil |
| 2,726,658 A | 12/1955 | Chessey |
| 3,244,210 A | 4/1966 | Giacomo |
| 3,463,161 A | 8/1969 | Andrassy |
| 3,587,577 A | 6/1971 | Smirnov et al. |
| 3,696,814 A | 10/1972 | Umemoto |
| 3,717,145 A | 2/1973 | Berndt et al. |
| 3,895,638 A | 7/1975 | Ito |
| 3,908,655 A | 9/1975 | Lund |
| 3,979,345 A | 9/1976 | Yates et al. |
| 3,988,568 A | 10/1976 | Mantell |
| 4,118,946 A | 10/1978 | Tubin |
| 4,172,495 A | 10/1979 | Zebuhr et al. |
| 4,204,543 A | 5/1980 | Henderson |
| 4,356,709 A | 11/1982 | Alexander |
| 4,425,916 A | 1/1984 | Bowen |
| 4,466,439 A | 8/1984 | Moore |
| 4,483,021 A | 11/1984 | McCall |
| 4,566,455 A | 1/1986 | Kramer |
| 4,574,411 A | 3/1986 | Yagi |
| 4,691,762 A | 9/1987 | Elkins et al. |
| 4,742,827 A | 5/1988 | Lipton |
| 4,753,242 A | 6/1988 | Saggers |
| 4,765,338 A | 8/1988 | Turner et al. |
| 4,781,193 A | 11/1988 | Pagden |
| 4,854,319 A | 8/1989 | Tobin |
| 4,891,501 A | 1/1990 | Lipton |
| 4,920,963 A | 5/1990 | Brader |
| 4,961,422 A | 10/1990 | Marchosky et al. |
| 5,097,828 A | 3/1992 | Deutsch |
| 5,097,829 A | 3/1992 | Quisenberry |
| 5,163,425 A | 11/1992 | Nambu et al. |
| 5,183,058 A | 2/1993 | Janese |
| 5,184,613 A | 2/1993 | Mintz |
| 5,197,466 A | 3/1993 | Marchosky et al. |
| 5,228,431 A | 7/1993 | Giarretto |
| 5,261,399 A | 11/1993 | Klatz et al. |
| 5,274,865 A | 1/1994 | Takehashi |
| 5,292,347 A | 3/1994 | Pompei |
| 5,305,470 A | 4/1994 | Mckay |
| 5,305,471 A | 4/1994 | Steele et al. |
| 5,314,456 A | 5/1994 | Cohen |
| 5,327,585 A | 7/1994 | Karlan |
| 5,342,411 A | 8/1994 | Maxted et al. |
| 5,344,437 A | 9/1994 | Pistay |
| 5,356,426 A | 10/1994 | Delk et al. |
| 5,400,617 A | 3/1995 | Ragonesi et al. |
| 5,409,500 A | 4/1995 | Dyrek |
| 5,441,476 A | 8/1995 | Kitado et al. |
| 5,469,579 A | 11/1995 | Tremblay et al. |
| 5,531,777 A | 7/1996 | Goldstein et al. |
| 5,545,199 A | 8/1996 | Hudson |
| 5,603,728 A | 2/1997 | Pachys |
| 5,609,619 A | 3/1997 | Pompei |
| 5,643,336 A | 7/1997 | Lopez-Claros |
| 5,658,324 A | 8/1997 | Bailey, Sr. et al. |
| 5,715,533 A | 2/1998 | Stein |
| 5,755,756 A | 5/1998 | Freedman, Jr. et al. |
| 5,837,002 A | 11/1998 | Augustine et al. |
| 5,848,981 A | 12/1998 | Herbranson |
| 5,867,999 A | 2/1999 | Bratton et al. |
| 5,871,526 A | 2/1999 | Gibbs et al. |
| 5,895,418 A | 4/1999 | Saringer |
| 5,897,581 A | 4/1999 | Fronda et al. |
| 5,897,582 A | 4/1999 | Agnatovech et al. |
| 5,916,242 A | 6/1999 | Schwartz |
| 5,948,012 A | 9/1999 | Mahaffey et al. |
| 5,950,234 A | 9/1999 | Leong et al. |
| 5,957,963 A | 9/1999 | Dobak, III |
| 5,957,964 A | 9/1999 | Ceravolo |
| 6,010,528 A | 1/2000 | Augustine et al. |
| 6,017,337 A | 1/2000 | Pira |
| 6,030,412 A | 2/2000 | Klatz et al. |
| 6,051,019 A | 4/2000 | Dobak, III |
| 6,083,254 A | 7/2000 | Evans |
| 6,113,626 A | 9/2000 | Clifton et al. |
| 6,126,680 A | 10/2000 | Wass |
| 6,156,057 A | 12/2000 | Fox |
| 6,156,059 A | 12/2000 | Olofsson |
| 6,183,501 B1 | 2/2001 | Latham |
| 6,197,045 B1 * | 3/2001 | Carson ............ A61F 7/02 601/148 |
| 6,228,376 B1 | 5/2001 | Misumi et al. |
| 6,231,595 B1 | 5/2001 | Dobak, III |
| 6,248,126 B1 | 6/2001 | Lesser et al. |
| 6,277,143 B1 | 8/2001 | Klatz et al. |
| 6,295,819 B1 | 10/2001 | Mathiprakasam et al. |
| 6,312,453 B1 | 11/2001 | Stefanile et al. |
| 6,363,285 B1 | 3/2002 | Wey |
| 6,375,673 B1 | 4/2002 | Clifton et al. |
| 6,375,674 B1 | 4/2002 | Carson |
| 6,409,746 B1 | 6/2002 | Igaki et al. |
| 6,416,532 B1 | 7/2002 | Fallik |
| 6,461,379 B1 | 10/2002 | Carson et al. |
| 6,500,201 B1 | 12/2002 | Tsuchiya et al. |
| 6,511,502 B2 | 1/2003 | Fletcher |
| 6,516,624 B1 | 2/2003 | Ichigaya |
| 6,523,354 B1 | 2/2003 | Tolbert |
| 6,551,347 B1 | 4/2003 | Elkins |
| 6,554,787 B1 | 4/2003 | Griffin et al. |
| 6,581,400 B2 | 6/2003 | Augustine et al. |
| 6,599,312 B2 | 7/2003 | Dobak, III |
| 6,610,084 B1 | 8/2003 | Torres |
| 6,629,990 B2 | 10/2003 | Putz et al. |
| 6,669,715 B2 | 12/2003 | Hoglund et al. |
| 6,673,098 B1 * | 1/2004 | Machold ............ A61F 7/123 607/104 |
| 6,682,552 B2 | 1/2004 | Ramsden et al. |
| 6,692,518 B2 | 2/2004 | Carson |

(56) References Cited

U.S. PATENT DOCUMENTS

| | | |
|---|---|---|
| 6,699,267 B2 | 3/2004 | Voorhees et al. |
| 6,736,837 B2 | 5/2004 | Fox |
| 6,740,109 B2 | 5/2004 | Dobak, III |
| 6,740,110 B2 | 5/2004 | Babcock |
| 6,770,085 B1 | 8/2004 | Munson |
| 6,845,520 B2 | 1/2005 | Kim |
| 6,854,128 B1 | 2/2005 | Faulk |
| 6,881,219 B1 | 4/2005 | Agarwal et al. |
| 6,921,374 B2 | 7/2005 | Augustine |
| 6,929,656 B1 | 8/2005 | Lennox |
| 6,962,600 B2 | 11/2005 | Lennox et al. |
| 6,979,345 B2 | 12/2005 | Werneth |
| 7,008,445 B2 | 3/2006 | Lennox |
| 7,044,960 B2 | 5/2006 | Voorhees et al. |
| 7,052,509 B2 | 5/2006 | Lennox et al. |
| 7,056,334 B2 | 6/2006 | Lennox |
| 7,077,858 B2 | 7/2006 | Fletcher et al. |
| 7,087,075 B2 | 8/2006 | Briscoe et al. |
| 7,146,211 B2 | 12/2006 | Frei et al. |
| 7,152,412 B2 | 12/2006 | Harvie |
| 7,179,280 B2 | 2/2007 | Mills |
| 7,182,777 B2 | 2/2007 | Mills |
| 7,189,252 B2 | 3/2007 | Krueger |
| 7,229,468 B2 | 6/2007 | Wong, Jr. et al. |
| 7,309,348 B2 | 12/2007 | Streeter et al. |
| 7,559,907 B2 | 7/2009 | Krempel et al. |
| 7,637,931 B2 | 12/2009 | Heaton |
| 7,744,640 B1 | 6/2010 | Faries, Jr. et al. |
| 7,854,754 B2 | 12/2010 | Ting et al. |
| 7,875,066 B2 | 1/2011 | Cohen et al. |
| 7,877,827 B2 | 2/2011 | Marquette et al. |
| 7,909,861 B2 | 3/2011 | Balachandran et al. |
| 7,930,772 B2 | 4/2011 | Fontanez |
| 8,052,624 B2 | 11/2011 | Buchanan et al. |
| 8,236,038 B2 | 8/2012 | Nofzinger |
| 8,425,583 B2 | 4/2013 | Nofzinger |
| 8,784,293 B2 | 7/2014 | Berka et al. |
| 9,089,400 B2 | 7/2015 | Nofzinger |
| 9,211,212 B2 * | 12/2015 | Nofzinger ............... A61F 7/007 |
| 9,492,313 B2 * | 11/2016 | Nofzinger ............... A61F 7/02 |
| 9,669,185 B2 * | 6/2017 | Nofzinger ............ A61M 21/02 |
| 2001/0000029 A1 | 3/2001 | Misumi et al. |
| 2001/0025191 A1 | 9/2001 | Montgomery |
| 2001/0039442 A1 | 11/2001 | Gorge et al. |
| 2001/0045104 A1 | 11/2001 | Bailey, Sr. et al. |
| 2002/0026226 A1 | 2/2002 | Ein |
| 2002/0095198 A1 | 7/2002 | Whitebook et al. |
| 2002/0103520 A1 | 8/2002 | Latham |
| 2002/0156509 A1 | 10/2002 | Cheung |
| 2003/0109911 A1 | 6/2003 | Lachenbruch et al. |
| 2003/0130651 A1 | 7/2003 | Lennox |
| 2003/0149461 A1 | 8/2003 | Johnson |
| 2003/0171685 A1 | 9/2003 | Lesser et al. |
| 2003/0195439 A1 | 10/2003 | Caselnova |
| 2004/0010178 A1 | 1/2004 | Buckner |
| 2004/0024432 A1 | 2/2004 | Castilla |
| 2004/0049134 A1 | 3/2004 | Tosaya et al. |
| 2004/0059400 A1 | 3/2004 | Lin |
| 2004/0064170 A1 | 4/2004 | Radons et al. |
| 2004/0073280 A1 | 4/2004 | Dae et al. |
| 2004/0073281 A1 | 4/2004 | Caselnova |
| 2004/0159109 A1 | 8/2004 | Harvie |
| 2004/0171970 A1 | 9/2004 | Schleuniger et al. |
| 2004/0186541 A1 | 9/2004 | Agarwal et al. |
| 2004/0249427 A1 | 12/2004 | Nabilsi |
| 2005/0065584 A1 | 3/2005 | Schiff et al. |
| 2005/0087194 A1 | 4/2005 | Scott |
| 2005/0107851 A1 | 5/2005 | Taboada et al. |
| 2005/0131504 A1 | 6/2005 | Kim |
| 2005/0143797 A1 | 6/2005 | Parish et al. |
| 2006/0024358 A1 | 2/2006 | Santini et al. |
| 2006/0122673 A1 * | 6/2006 | Callister ............... A61F 7/12 607/105 |
| 2006/0149119 A1 | 7/2006 | Wang |
| 2006/0161230 A1 | 7/2006 | Craven |
| 2006/0173396 A1 | 8/2006 | Hatamian et al. |
| 2006/0198874 A1 | 9/2006 | Stanley |
| 2006/0235495 A1 | 10/2006 | Tsai |
| 2006/0235498 A1 | 10/2006 | Mollendorf et al. |
| 2006/0293732 A1 | 12/2006 | Collins et al. |
| 2007/0010861 A1 | 1/2007 | Anderson et al. |
| 2007/0055330 A1 | 3/2007 | Rutherford |
| 2007/0123758 A1 | 5/2007 | Miesel et al. |
| 2007/0207220 A1 | 9/2007 | Luedtke et al. |
| 2007/0250138 A1 * | 10/2007 | Nofzinger ............... A61F 7/10 607/96 |
| 2007/0282249 A1 | 12/2007 | Quisenberry et al. |
| 2007/0282406 A1 | 12/2007 | Dow |
| 2008/0015665 A1 | 1/2008 | Lachenbruch |
| 2008/0033518 A1 | 2/2008 | Rousso et al. |
| 2008/0046026 A1 | 2/2008 | Pless et al. |
| 2008/0046047 A1 | 2/2008 | Jacobs |
| 2008/0097560 A1 | 4/2008 | Radziunas et al. |
| 2008/0097561 A1 | 4/2008 | Melsky et al. |
| 2008/0103568 A1 | 5/2008 | Dow |
| 2008/0140096 A1 | 6/2008 | Svadovskiy |
| 2008/0168605 A1 | 7/2008 | Wolske |
| 2008/0188915 A1 | 8/2008 | Mills et al. |
| 2008/0228248 A1 | 9/2008 | Guyuron et al. |
| 2008/0249520 A1 | 10/2008 | Dunning et al. |
| 2008/0269852 A1 | 10/2008 | Lennox et al. |
| 2008/0288033 A1 | 11/2008 | Mason et al. |
| 2008/0300529 A1 | 12/2008 | Reinstein |
| 2009/0024043 A1 | 1/2009 | MacLeod et al. |
| 2009/0049694 A1 | 2/2009 | Morris |
| 2009/0054958 A1 | 2/2009 | Nofzinger |
| 2009/0198311 A1 | 8/2009 | Johnson et al. |
| 2009/0236893 A1 | 9/2009 | Ehlers et al. |
| 2009/0306748 A1 | 12/2009 | Mollendorf et al. |
| 2009/0312676 A1 | 12/2009 | Rousso et al. |
| 2009/0312823 A1 | 12/2009 | Patience et al. |
| 2010/0030306 A1 | 2/2010 | Edelman et al. |
| 2010/0087701 A1 | 4/2010 | Berka et al. |
| 2010/0122398 A1 | 5/2010 | Luciano |
| 2010/0198281 A1 | 8/2010 | Chang et al. |
| 2010/0198318 A1 | 8/2010 | Rogers |
| 2010/0211142 A1 | 8/2010 | Rogers et al. |
| 2010/0241200 A1 | 9/2010 | Bruder et al. |
| 2010/0312317 A1 | 12/2010 | Baltazar |
| 2010/0331752 A1 | 12/2010 | Cumming et al. |
| 2011/0125233 A1 | 5/2011 | Shen et al. |
| 2011/0125238 A1 * | 5/2011 | Nofzinger ............... A61F 7/10 607/109 |
| 2011/0184502 A1 | 7/2011 | Bruder |
| 2011/0282269 A1 | 11/2011 | Quisenberry et al. |
| 2012/0150268 A1 | 6/2012 | Doherty et al. |
| 2012/0302942 A1 | 11/2012 | DiPierro et al. |
| 2012/0310312 A1 | 12/2012 | Yee |
| 2013/0007945 A1 | 1/2013 | Krondahl |
| 2013/0103125 A1 | 4/2013 | Radspieler et al. |
| 2013/0131464 A1 | 5/2013 | Westbrook et al. |
| 2013/0202668 A1 | 8/2013 | Prost et al. |
| 2013/0238063 A1 * | 9/2013 | Nofzinger ............... A61F 7/10 607/104 |
| 2013/0289680 A1 | 10/2013 | Hasegawa |
| 2014/0303698 A1 | 10/2014 | Benyaminpour et al. |
| 2014/0343069 A1 | 11/2014 | Laiji et al. |
| 2015/0018905 A1 | 1/2015 | Nofzinger et al. |
| 2015/0238725 A1 | 8/2015 | Tucker et al. |
| 2015/0290420 A1 * | 10/2015 | Nofzinger ............... A61F 7/10 600/27 |
| 2016/0128864 A1 | 5/2016 | Nofzinger et al. |
| 2017/0252534 A1 | 9/2017 | Nofzinger |
| 2017/0319815 A1 | 11/2017 | Nofzinger et al. |
| 2017/0333667 A1 | 11/2017 | Tucker |

FOREIGN PATENT DOCUMENTS

| | | |
|---|---|---|
| GB | 460200 A | 1/1937 |
| GB | 461294 A | 2/1937 |
| JP | (UM)2-20522 | 2/1990 |
| JP | 10-192331 | 7/1998 |
| JP | 11-042282 | 2/1999 |

(56) References Cited

FOREIGN PATENT DOCUMENTS

| | | |
|---|---|---|
| JP | 2003164496 | 6/2003 |
| JP | 2004189999 A | 7/2004 |
| JP | 3730096 B | 10/2005 |
| JP | 2005274013 | 10/2005 |
| JP | 2006102020 | 4/2006 |
| JP | 20007175476 A | 7/2007 |
| WO | WO90/01911 A1 | 3/1990 |
| WO | WO92/20309 A1 | 11/1992 |
| WO | WO94/00086 A1 | 1/1994 |
| WO | WO95/10251 A1 | 4/1995 |
| WO | WO96/10379 A2 | 4/1996 |
| WO | WO96/31136 A1 | 10/1996 |
| WO | WO97/36560 A1 | 10/1997 |
| WO | WO98/56310 A1 | 12/1998 |
| WO | WO99/08632 A1 | 2/1999 |
| WO | WO00/03666 A1 | 1/2000 |
| WO | WO00/09052 A1 | 2/2000 |
| WO | WO01/39704 A1 | 6/2001 |
| WO | WO02/05736 A2 | 1/2002 |
| WO | WO02/34177 A1 | 5/2002 |
| WO | WO03/092539 A2 | 11/2003 |
| WO | WO2004/065862 A2 | 8/2004 |
| WO | WO2004/111741 A1 | 12/2004 |
| WO | WO2005/007060 A2 | 1/2005 |
| WO | WO2005/076806 A2 | 8/2005 |
| WO | WO2005/120428 A1 | 12/2005 |
| WO | WO2006/073915 A2 | 7/2006 |
| WO | WO2006/086086 A2 | 8/2006 |
| WO | WO2007/005026 A1 | 1/2007 |
| WO | WO2007/101039 A1 | 9/2007 |
| WO | WO2008/099017 A1 | 8/2008 |
| WO | WO2008/129357 A2 | 10/2008 |
| WO | WO2008/142650 A1 | 11/2008 |
| WO | WO2008/151260 A2 | 12/2008 |
| WO | WO2009/073208 A1 | 6/2009 |
| WO | WO2009/122336 A1 | 10/2009 |
| WO | WO2009/147413 A1 | 12/2009 |
| WO | WO2011/161571 A1 | 12/2011 |
| WO | WO2012/012683 A1 | 1/2012 |
| WO | WO2012/028730 A1 | 3/2012 |
| WO | WO2012/083151 A1 | 6/2012 |
| WO | WO2015/071810 A1 | 5/2015 |

OTHER PUBLICATIONS

Adam et al.; Physiological and psychological differences between good and poor sleepers; J. psychiat. Res.; 20(4); pp. 301-316; 1986 (year of pub. sufficiently earlier than effective US filing date and any foreign priority date).
Ahiska et al.; Control of a thermoelectric brain cooler by adaptive neuro-fuzzy interference system; Instrumentation Science and Technology; vol. 36(6); pp. 636-655; Oct. 2008.
Ahmed et al.; Development of a cooling unit for the emergency treatment of head injury; World Congress on Medical Physics and Biomedical Engineering 2006; IFMBE Proceedings; vol. 14(5); Track 19; pp. 3243-3246; Aug. 2006 (copyright 2007).
Alam et al.; Local preoptic / anterior hypothalamic warming alters spontaneous and evoked neuronal activity in the magno-cellular basal forebrain; Brian Research; 696; pp. 221-230; Oct. 1995.
Alam et al.; Preoptic / anterior hypothalamic neurons: thermosensitivity in rapid eye movement sleep; Am. J. Physiol. Regul. Integr. Comp. Physiol.; 269; pp. R1250-R1257; Nov. 1995.
Alfoldi et al.; Brian and core temperatures and peripheral vasomotion during sleep and wakefulness at various ambient temperatures in the rat; Pflugers Arch.; 417; pp. 336-341; Nov. 1990.
Aschoff, Circadian Rhythms in Man, Science, vol. 148, pp. 1427-1432, Jun. 11, 1965.
Baker et al.; Persistence of sleep-temperature coupling after suprachiasmatic nuclei lesions in rats; Am. J. Physiol. Regul. Integr. Comp. Physiol.; 289(3); pp. R827-R838; Sep. 2005.
Boulant et al.; Hypothalamic neuronal responses to peripheral and deep-body temperatures; Am. J. of Physiol.; 225(6); pp. 1371-1374; Dec. 1973.

Boulant et al.; Temperature receptors in the central nervous system; Ann. Rev. Physiol.; 48; pp. 639-654; 1986 (year of pub. sufficiently earlier than effective US filing date and any foreign priority date).
Boulant et al.; The effects of spinal and skin temperatures on the firing rate and thermosensitivity of preoptic neurones; J. Physiol.; 240(3); pp. 639-660; Aug. 1974.
Boulant; Hypothalamic mechanisms in thermoregulation; Fed. Proc.; 40(14); pp. 2843-2850; Dec. 1981.
Brown; Toe temperature change: a measure of sleep onset?; Walking and Sleeping; 3(4); pp. 353-359; Sep.-Dec. 1979.
Clarkson et al.; Thermal neutral temperature of rats in helium-oxygen, argon-oxygen, and air; Am. J. Physiol.; 222(6); pp. 1494-1498; Jun. 1972.
Crawshaw et al.; Effect of local cooling on sweating rate and cold sensation; Pfugers Arch.; 354(1); pp. 19-27; 1975 (year of pub. sufficiently earlier than effective US filing date and any foreign priority date).
Diao et al., Cooling and Rewarming for Brain Ischemia or Injury: Theoretical Analysis, Annals of Biomedical Engineering, vol. 31, p. 346-353, Mar. 2003.
Gong et al.; Sleep-related c-Fos protien expression in the preoptic hypothalamus: effects of ambient warming; Am. J. Physiol. Regul. Integr. Comp. Physiol.; 279(6); pp. R2079-R2088; Dec. 2000.
Gordon; Relationship between preferred ambient temperature and autonomic thermoregulatory function in rat; Am. J. Physiol. Regul. Integr. Comp. Physiol.; 252; pp. R1130-R1137; 1987 (year of pub. sufficiently earlier than effective US filing date and any foreign priority date).
Gulia et al.; Ambient temperature related sleep changes in rats neonatally treated with capsaicin; Physiol. Behav.; 85(4); pp. 414-418; Jul. 21, 2005.
Guzman-Marin et al.; Discharge modulation of rat dorsal raphe neurons during sleep and waking: effects of preoptic / basal forebrain warming; Brain Res.; 875(1-2); pp. 23-34; Sep. 1, 2000.
Hajos et al.; The capsaicin sensitivity of the preoptic region is preserved in adult rats pretreated as neonates, but lost in rats pretreated as adults; Naunyn-Schmiedeberg's Arch. Pharmacol.; 324(3); pp. 219-222; Nov. 1983.
Haskell et al.; The effects of high and low ambient temperatures on human sleep stages; Electroencephalogr. Clin. Neurophysiol.; 51(5); pp. 494-501; May 1981.
Hayashi et al., The alerting effects of caffeine, bright light and face washing after a short daytime nap, Clinical Neurophysiology, 114(12), pp. 2268-2278, Dec. 2003.
Hensley et al.; 50 years of computer simulation of the human thermoregulatory system; J. Biomech. Eng.; 135(2); pp. 021005-1-021005-9; Feb. 2013.
Herrington; The heat regulation of small laboratory animals at various environmental temperatures; Am. J. of Physiol.; 129; pp. 123-139; Mar. 31, 1940.
Heuvel et al.; Changes in sleepiness and body temperature precede nocturnal sleep onset: evidence from a polsomnographic study in young men; J. Sleep Res.; 7(3); pp. 159-166; Sep. 1998.
Horne et al., Vehicle accidents related to sleep: a review, Occup Environ Med, vol. 56(5), pp. 289-294 (full text version 13 pgs.), May 1999.
Horne et al.; Exercise and sleep: body-heating effects; Sleep; 6(1); pp. 36-46; 1983 (year of pub. sufficiently earlier than effective US filing date and any foreign priority date).
Horne et al.; Slow wave sleep elevations after body heating: proximity to sleep and effects of aspirin; Sleep; 10(4); pp. 383-392; Aug. 1987.
Iber et al.; The AASM manual for the scoring of sleep and associatted events. the rules, terminology and technical specifications; Westchester, IL; © 2007; 57 pages; Oct. 28, 2014; retrieved from the internet (http://www.nswo.nl/userfiles/files/AASM%20-%20Manual%20for%20the%20Scoring%20ofSleep%20and%20Associated%20Events%20-%2005-2007_2.pdf).
Iwata et al., Brain temperature in newborn piglets under selective head cooling with minimal systemic hypothermia, Pediatrics International, 45(2), pp. 163-168; Apr. 2003.

(56) References Cited

OTHER PUBLICATIONS

John et al.; Changes in sleep-wakefulness after kainic acid lesion of the preoptic area in rats; Jpn J. Physiol.; 44; pp. 231-242; 1994 (year of pub. sufficiently earlier than effective US filing date and any foreign priority date).
John et al.; Effect of NMDA lesion of the medial preoptic neurons on sleep and other functions; Sleep; 21(6); pp. 587-598; Sep. 15, 1998.
Khubchandani et al.; Functional MRI shows activation of the medial preoptic area during sleep; NeuroImage; 26; pp. 29-35; May 15, 2005.
Krauchi et al., Circadian rhythm of heat production, heart rate, and skin and core temperature under unmasking conditions in men, American Physiological Society, 267 (3 Pt 2), pp. R819-R829, Sep. 1994.
Krauchi et al., Circadian Clues to Sleep Onset Mechanisms, Neuropsychopharmacology, vol. 25, No. S5, pp. S92-S96, Nov. 2001.
Krauchi et al., Functional link between distal vasodilation and sleep-onset latency, Am. J. Physiol. Regulatory Integrative Comp. Physiol., 278(3), pp. R741-R748, Mar. 2000.
Krauchi et al., Warm feet promote the rapid onset of sleep, Nature, vol. 401, pp. 36-37, Sep. 2, 1999.
Krilowicz et al.; Regulation of posterior lateral hypothalamic arousal related neuronal discharge by preoptic anterior hypothalamic warming; Brain Res.; 668(1-2); pp. 30-38; Dec. 30, 1994.
Kumar et al.; Ambient temperature that induces maximum sleep in rats; Physiol. Behav.; 98(1-2); pp. 186-191; Aug. 4, 2009.
Kumar et al.; Ambient temperature-dependent thermoregulatory role of REM sleep; Journal of Thermal Biology; 37(5); pp. 392-396; Aug. 2012.
Kumar et al.; Warm sensitive neurons of the preoptic area regulate ambient temperature related changes in sleep in the rat; Indian J. Physiol. Pharmacol.; 55(3); pp. 262-271; Jul.-Sep. 2011.
Kumar; Body temperature and sleep: are they controlled by the same mechanism?; Sleep and Biological Rhythms; 2(2); pp. 103-124; Jun. 2004.
Lack et al.; The rhythms of human sleep propensity and core body temperature; J. Sleep Res.; 5(1); pp. 1-11; Mar. 1996.
Lee et al.; Thermal spot over human body surface (part 1) regional difference in cold spot distribution; J. Human and Living Environment; 2(1); pp. 30-36; 1995 (year of pub. sufficiently earlier than effective US filing date and any foreign priority date).
Leshner et al., Manifestations and Management of Chronic Insomnia in Adults, NIH State-of-the-Science Conference, Final Panel Statement, Bethesda, MD, 36 pgs., Jun. 13-15, 2005.
Libert et al.; Effect of continuous heat exposure on sleep stages in humans; Sleep; 11(2); pp. 195-209; Apr. 1988.
Lu et al.; Effect of lesions of the ventrolateral preoptic nucleus on NREM and REM sleep; J. Neurosci.; 20(10); pp. 3830-3842; May 15, 2000.
Mahapatra et al.; Changes in sleep on chronic exposure to warm and cold ambient temperatures; Physiol. Behav.; 84(2); pp. 287-294; Feb. 15, 2005.
McGinity et al.; Hypothalamic regulation of sleep and arousal; Frontiers in Bioscience; 8; pp. s1074-s1083; Sep. 1, 2003.
McGinity et al., Keeping cool: a hypothesis about the mechanisms and functions of slow-wave sleep; TINS; 13(12); pp. 480-487; Dec. 1990.
McGinity et al.; Sleep suppression after basal forebrain lesions in the cat; Science; 160(3833); pp. 1253-1255; Jun. 14, 1968.
McKenzie/Mini-Mitter Co.; Mini-Logger® Series 2000, Physiological Data Logging Device; 510K Summary and Premarket Notification (No. K033534); 10 pgs.; Apr. 22, 2004.
Methipara et al.; Preoptic area warming inhibits wake-active neurons in the perifornical lateral hypothalamus; Brain Res.; 960(1-2); pp. 165-173; Jan. 17, 2003.
Morairty et al.; Selective increases in non-rapid eye movement sleep following whole body heating in rats; Brain Res.; 617(1); pp. 10-16; Jul. 16, 1993.

Nadel et al.; Differential thermal sensitivity in the human skin; Pflugers Arch.; 340(1); pp. 71-76; 1973 (year of pub. sufficiently earlier than effective US filing date and any foreign priority date).
Nakamura; Central circuitries for body temperature regulation and fever; Am. J. Physiol. Regul. Integr. Comp. Phsiol.; 301(5); pp. R1207-R1228; Nov. 2011.
Nakayama et al.; Thermal stimulation of electrical activity of single units of the preoptic region; Am. J. Physiol.; 204(6); pp. 1122-1126; 1963 (year of pub. sufficiently earlier than effective US filing date and any foreign priority date).
Nakayama; Single unit activity of anterior hypothalamus during local heating; Science; 134(3478); pp. 560-561; Aug. 25, 1961.
Nauta; Hypothalamic regulation of sleep in rats. An experimental study; J. Neurophysiol.; 9; pp. 285-316; Jul. 1946.
Nofzinger et al., Functional Neuroimaging Evidence for Hyperarousal in Insomnia, Am J Psychiatry, 161(11), pp. 2126-2128, Nov. 2004.
Nofzinger et al.; Alterations in regional cerebral glucose metabolism across waking and non-rapid eye movement sleep in depression; Arch. Gen. Psychiatry; 62(4); pp. 387-396; Apr. 2005.
Nofzinger et al.; Frontal cerebral hypothermia: A new approach to the treatment of insomnia; Sleep; Abstract Suppl.; vol. 32; abstract No. 0881; pp. A287-A288; Jun. 2009.
Nofzinger et al.; Frontal cerebral thermal transfer as a treatment for insomnia: A dose-ranging study; Sleep; Abstract Suppl.; vol. 34; abstract No. 0534; p. A183; Jun. 2011.
Nofzinger et al.; Regional cerebral metabolic correlates of WASO during NREM sleep in insomnia; J. Clinical Sleep Med.; 2(3); pp. 316-322; Jul. 2006.
Nofzinger/Cereve; SBIR/STTR Grant Submission; Feasibility of frontal cerebral hypothermia as a treatment for insomnia; submitted Dec. 9, 2008.
Obal et al.; Changes in the brain and core temperatures in relation to the various arousal states in rats in the light and dark periods of the day; Pflugers Arch.; 404(1); pp. 73-79; May 1985.
Olympic Medical; Olympic Cool-Cap System (Product Brochure); 4 pgs.; (year of pub. sufficiently earlier than effective US filing date and any foreign priority date) 2007.
Osborne et al.; Effects of hypothalamic lesions on the body temperature rhythm of the golden hamster; Neuroreport; 6(16); pp. 2187-2192; Nov. 13, 1995.
Parmeggiani et al; Hypothalamic temperature during the sleep cycle at different ambient temperatures; Electroencephalogr. and Clin. Neurophysiol.; 38(6); pp. 589-596; Jun. 1975.
Parmeggiani; Interaction between sleep and thermoregulation: an aspect of the control of behavioral states; Sleep; 10(5); pp. 426-435; Oct. 1987.
Parmeggiani et al.; Sleep and environmental temperature; Arch. Ital. Biol.; 108(2); pp. 369-387; Apr. 1970.
Poole et al.; Body temperature regulation and thermoneutrality in rats; Q. J. Exp. Physiol. Cogn. Med. Sci.; 62(2); pp. 143-149; Apr. 1977.
Ray et al.; Changes in sleep-wakefulness in the medial preoptic area lesioned rats: role of thermal preference; Behav. Brain Res.; 158(1); pp. 43-52; Mar. 7, 2005.
Ray et al.; Changes in thermal preference, sleep-wakefulness, body temperature and locomotor activity of rats during continuous recording for 24 hours; Behav. Brain Res.; 154(2); pp. 519-526; Oct. 5, 2004.
Raymann et al.; Diminished capability to recognize the optimal temperature for sleep initiation may contribute to poor sleep in elderly people; Sleep; 31(9); pp. 1301-1309; Sep. 2008.
Raymann et al.; Skin deep: enhanced sleep depth by cutaneous temperature manipulation; Brain; 131(PT 2); pp. 500-513; Feb. 2008.
Reyner et al., Evaluation of 'In-Car' Countermeasures to Sleepiness: Cold Air and Radio, Sleep, vol. 21(1), pp. 46-50, (year of pub. sufficiently earlier than effective US filing date and any foreign priority date) 1998.
Romanovsky et al.; Molecular biology of thermoregulation selected contribution: ambient temperature for experiments in rats: a new method for determining the zone of thermal neutrality; J. Appl. Phsyiol.; 92(6); pp. 2667-2679; Jun. 2002.

(56) References Cited

OTHER PUBLICATIONS

Schmidek et al.; Influence of environmental temperature on the sleep-wakefulness cycle in the rat; Physiol. Behav.; 8(2); pp. 363-371; Feb. 1972.
Setokawa et al.; Facilitating effect of cooling the occipital region on nocturnal sleep; Sleep and Biological Rhythms; 5(3); pp. 166-172; Jul. 2007.
Sewitch; Slow wave sleep deficiency insomnia: a problem in thermo-downregulation at sleep onset; Phychophsyiology; 24(2); pp. 200-215; Mar. 1987.
Shapiro et al.; Thermal load alters sleep; Biol. Psychiatry; 26(7); pp. 736-740; Nov. 1989.
Sherin et al.; Activation of ventrolateral preoptic neurons during sleep; Science; 271(5246); pp. 216-219; Jan. 12, 1996.
Srividya et al.; Differences in the effects of medial and lateral preoptic lesions on thermoregulation and sleep in rats; Neuroscience; 139(3); pp. 853-864; 2006 (year of pub. sufficiently earlier than effective US filing date and any foreign priority date).
Srividya et al.; Sleep changes produced by destruction of medial septal neurons in rats; Neororeport; 15(11); pp. 1831-1835; Aug. 2004.
Sterman e tal.; Forebrain inhibitory mechanisms: sleep patterns induced by basal forebrain stimulation in the behaving cat; Exp. Neurol.; 6; pp. 103-117; Aug. 1962.
Stevens et al.; Regional sensitivity and spatial summation in the warmth sense; Physiol. Behav.; 13(6); pp. 825-836; Dec. 1974.
Stevens et al.; Temperature sensitivity of the body surface over the life span; Somatosens. Mot. Res.; 15(1); pp. 13-28; 1998 (year of pub. sufficiently earlier than effective US filing date and any foreign priority date).
Szymusiak et al.; Ambient temperature-dependence of sleep disturbances produced by basal forebrain damage in rats; Brain Res. Bull.; 12(3); pp. 295-305; Mar. 1984.
Szymusiak et al.; Maximal REM sleep time defines a narrower thermoneutral zone than does minimal metabolic rate; Physiol. Behav.; 26(4); pp. 687-690; Apr. 1981.
Szymusiak et al.; Sleep suppression following kainic acid-induced lesions of the basal forebrain; Exp. Neurol.; 94(3); pp. 598-614; Dec. 1986.
Szymusiak et al.; Sleep-related neuronal discharge in the basal forebrain of cats; Brain Res.; 370(1); pp. 82-92; Apr. 2, 1986.
Tamura et al.; Thermal spot over human body surface (part II) regional diference in warm spot distribution; J. Human and Living Environment; 2(1); pp. 37-42; 1995 (year of pub. sufficiently earlier than effective US filing date and any foreign priority date).
Thannickal et al.; Effect of ambient temperature on brain temperature and sleep-wakefulness in medial preoptic area lesioned rats; Indian J. Pharmacol.; 46(3); pp. 287-297; Jul. 2002.
Van Someren; Mechanisms and functions of coupling between sleep and temperature rhythms; Progress in Brain research; 153; pp. 309-324; 2006 (year of pub. sufficiently earlier than effective US filing date and any foreign priority date).
Van Someren; More than a maker: interaction between the ciradian regulation of temperature and sleep, age-related changes, and treatment possibilities; Chronobiol. Int.; 17(3); pp. 313-354; May 2000.
Von Economo; Sleep as a problem of localization; The Journal of Nervous and Mental Disease; 71(3); pp. 1-5; Mar. 1930.
Wang et al., Rapid and selective cerebral hypothermia achieved using a cooling helmet, Journal of Neurosurgery, vol. 100 No. 2, pp. 272-277 (full text version 18 pgs), Feb. 2004.
Yavuz et al.; Thermoelectric brain cooler helmet; 6th International Advanced Technologies Symposium (IATS'11); Elazig, Turkey; pp. 120-123; May 16-18, 2011.
Mallick et al; Basal forebrain thermoregulatory mechanism modulates auto-regulated sleep; Frontiers in Neurology; 10.3389/fneur. 2012.00102 (8 pages); Jun. 27, 2012.

\* cited by examiner

SYSTEMS FOR ENHANCING SLEEP

CROSS REFERENCE TO RELATED APPLICATIONS

This patent application claims priority to U.S. provisional patent application 61/748,409, titled "SYSTEMS AND METHODS FOR ENHANCING SLEEP," filed 2 Jan. 2013, and U.S. provisional patent application No. 61/859,161, titled "APPARATUS AND METHOD FOR MODULATING SLEEP," filed 26 Jul. 2013. These provisional patent applications are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The devices and systems described herein generally relate to apparatuses (e.g., devices and systems) and methods for improving sleep (including reducing sleep onset and maintenance of sleep duration), enhancing, or increasing sleep, including, but not limited to, treating sleeping disorders such as insomnia.

BACKGROUND

Although sleep disruption and irregularities, including insomnia, are a widespread and pervasive problem, there are few systems for the treatment and/or enhancement of sleep. The systems and methods described herein address this need.

SUMMARY OF THE DISCLOSURE

Apparatuses, including systems and devices, for enhancing sleep, reducing sleep onset, increasing total sleep time, treating insomnia and treating other neurological disorders by applying noninvasive regional thermal stimulus to the subject's frontal cortex may include a thermal applicator that is configured to precisely control the application of a predetermined level of thermal energy to a specified region of a subject's head for a predetermined amount of time. This control may provide optimal treatment to enhance sleep, reduce sleep onset, or treat the subject for sleep-related disorders.

Generally, the apparatuses described herein may include a thermal applicator configured to attach to the subject's head, and a regulator coupled to the thermal applicator and configured to control the application of thermal energy to the subject through the applicator. A headgear may also be used. The thermal applicator may be configured to attach to a subject's head to specifically deliver thermal regulation to the region of the subject's head over the frontal/prefrontal cortex; the thermal applicator may be specifically configured to limit the active application of thermal energy to this region (e.g., preventing active regulation of other, adjacent, regions, such as the eye orbit regions, etc.).

Any of the apparatuses described herein may be configured as clock (e.g., alarm-clock) devices that integrate an alarm clock capability with regulation of a subject's sleep. In particular, the apparatuses described herein may function as a clock that can display the time, encourage and/or enhance sleep (e.g., decreasing sleep onset time), and/or be programmed with an alarm or wake-up function that enhances the comfort of waking up. For example, any of the apparatuses described herein may be configured to allow a user to program a desired sleep time (e.g., go to bed time) and/or a desired wakeup time. The controller may activate the application of temperature regulation to enhance sleep and/or sleep onset at the desired on time, and may also modify the regulation of temperature at or before the desired wake-up time, e.g., by changing the temperature to transition from a sleep maintenance temperature to a wake-up temperature. The wake-up temperature may be selected to provide a more comfortable transition from sleep to wakefulness (e.g., at or near ambient temperature).

Any of the apparatuses described herein may also or alternatively include a cartridge, which may be removable, that contains a reservoir of thermal transfer fluid (e.g., water); the cartridge may provide thermal transfer fluid that is not thermally regulated to the pool of thermal transfer fluid within the thermal regulator unit that is thermally regulated. Thus, the apparatus may only thermally regulate (heat and/or cool) the thermal transfer fluid that is within the internal reservoir of the thermal regulator (e.g., in the internal plumbing of the thermal regulator).

A cartridge may be vented and/or at least partially collapsible to allow fluid to exit the reservoir of the cartridge and into the thermally regulated portion (e.g., internal plumbing) of the thermal regulator. For example, the cartridge may be collapsible chamber held within a rigid (non-collapsing) framework; the collapsible chamber may be filled with thermal transfer fluid. For example, the cartridge may be a bag within a housing (e.g., box). The bag may be unvented. In some variations the cartridge includes a valve; in variations including a valve, the valve may be configured to prevent fluid from leaking out of the cartridge, when it is not engaged with the internal reservoir of the thermal regulator unit.

In general, the apparatuses described herein may be configured to encourage or enhance sleep. Thus, these apparatus may be adapted to be quiet (e.g., operating at less than 40 dB SPL, or approximately ¼ as loud as an ordinary spoken conversation, +/−10 dB SPL). The apparatus may be adapted to provide a masking noise (e.g., music, white noise, etc.).

Any of the apparatuses described herein may also be configured to allow selection of an operating profile from a menu of profiles. The profiles may include the profile of thermal regulation applied to control the temperature of the thermal applicator, by regulating the temperature of the thermal transfer fluid. In some variation the profile includes one or more of: a (first) holding temperature, a ramp time to ramp from ambient temperature to the holding temperature, a duration of holding temperature, etc. The temperature may correspond to the actual temperature of the thermal transfer fluid or the temperature of the thermal applicator. Thus, in some variations the controller receives input from one or more sensors sensing the temperature of either or both the thermal transfer fluid and/or the thermal applicator, and may regulate the temperature accordingly (e.g., closed loop). Alternatively, the controller may be an open-loop controller.

In general, the thermal applicator may be configured, alone or in conjunction with a headgear to help hold the thermal applicator against the subject, to transfer thermal energy only between a portion or region of a subject's head and the thermal applicator. In particular, the thermally controlled region of the subject's head may correspond to the regions over the frontal and/or prefrontal cortex (e.g., the forehead). The thermal applicator and/or headgear may be thermally insulated to prevent transfer of thermal energy between the thermal transfer fluid and regions of the subject's head and/or body outside of the target region, such as the eyes, orbits of the eyes, cheeks, back of the head, ears, etc. The thermal applicator may be adapted to thermally regulate only the region of the subject's head over the prefrontal and frontal cortex, but not other regions of the subject's head and face including the eye orbits.

For example, a thermal system for enhancing a subject's sleep may include a thermal regulator unit having a housing, the thermal regulator unit configured to control the temperature of a thermal transfer fluid; a clock coupled with the thermal regulator unit; a display coupled with clock and the thermal regulator unit; a thermal applicator configured to be worn against a subject's forehead over the subject's prefrontal and frontal cortex, wherein the thermal applicator is configured to pass thermal transfer fluid from the thermal regulator unit; a controller within the thermal regulator unit configured to regulate the temperature of the thermal transfer fluid based on one or more thermal control profiles to modulate the subject's sleep by controlling a temperature of the thermal applicator; and a headgear to maintain the thermal applicator in contact with the region of the subject's head over the prefrontal and frontal cortex.

The controller may be configured to receive input from the clock and to modify the temperature of the thermal transfer fluid at a predetermined wakeup time to wake the subject. For example, the subject may use the clock as an alarm clock to determine the on time for the apparatus to apply thermal energy to enhance/encourage sleep and/or a wakeup time for the apparatus to regulate the temperature to a comfortable wake-up temperature. The alarm clock may also be configured to allow the user to set an alarm (visible, audible, or both).

The controller may be configured to maintain the temperature of the thermal transfer fluid so that the temperature of the thermal applicator at a target temperature selected from the range consisting of: about 10 degrees C. to about 41 degrees C. The apparatus may hold the thermal transfer fluid (and thus, the applicator) at a predetermined temperature or series of predetermined temperature for a predetermined time, and/or it may transition (e.g., ramp) the temperature to (or between) predetermined temperatures over a predetermined time duration. In some variations, the predetermined temperatures and/or predetermined durations may be set or selected by a user, and may form one or more profiles. The apparatus may be configured to allow a user to select from a plurality of profiles. The profiles may be described to the user explicitly (e.g., including temperature and time durations) or they may be described by ranked levels (e.g., more or less aggressive/intense), or by desired effect. For example, the controller may include a plurality of thermal control profiles configured to cause the controller to regulate that temperature of the thermal transfer fluid. The apparatus may include one or more controls in communication with the thermal regulator unit configured to allow the subject to select the one or more thermal control profiles.

In general, the apparatus may include a cooling and/or heating unit for regulating the temperature of the thermal transfer fluid and/or applicator. For example, the thermal regulator unit may comprise a thermal electric module configured to heat, cool, or heat and cool the thermal transfer fluid. The thermal regulator unit may be Peltier device, a thermoelectric heater (e.g., resistive heater), an evaporative cooler, a fan, or the like.

As mentioned, the apparatus may be configured to regulate a relatively small "pool" of thermal transfer fluid, while including a separate (not thermally regulated) reservoir of thermal transfer fluid that can be added to the pool to keep a minimum level of thermal transfer fluid. In some variations the apparatus includes a cartridge containing thermal transfer fluid adapted to be coupled to the thermal regulator unit; the cartridge may store the reservoir of thermal transfer fluid that is not thermally regulated.

Any of the apparatuses described herein may include tubing or other flexible, conduit for thermal transfer fluid to be passed to/from the thermal applicator and the thermal regulator unit. For example, the apparatus may include a fluid conduit connecting the thermal regulator unit and the thermal applicator, the fluid conduit configured to transfer thermal transfer fluid between the thermal regulator unit and the thermal applicator. The conduit may be tubing. The conduit may be insulated (thermally insulated) and leak-proof.

The apparatus may also include a fluid level detector within the thermal regulator unit configured to monitor the level of thermal transfer fluid within the system. This fluid level detector may be coupled to the controller or it may be directly or indirectly coupled to a reservoir, and may trigger the addition of fluid into the internal plumbing (the internal reservoir or pool of thermal transfer fluid that is thermally regulated).

Any of the apparatuses described may include a headgear to help hold the thermal applicator to the appropriate portion of the user's anatomy (e.g., head/forehead). For example, a headgear may be configured to maintain the thermal applicator in contact with just the region of the subject's head over the prefrontal and frontal cortex. The headgear may connect to the thermal applicator; in some variations the headgear is integrated with the thermal applicator (e.g., the thermal applicator includes one or more straps or other attachment mechanisms. The headgear may be adjustable and may be adapted to thermally insulate the thermal applicator from other, non-target regions of the subject's body.

As mentioned, the thermal regulator unit may include a first reservoir of thermal transfer fluid within an internal plumbing of the thermal regulator that is configured to be thermally regulated by a thermal electric module of the thermal regulator unit and a second reservoir of thermal transfer fluid that is not thermally regulated by the thermal electric module, and a valve configured to transfer fluid between the first reservoir and the second reservoir to maintain a level of thermal transfer fluid within the first reservoir.

Any of the apparatuses described herein may include a display. The display may be a "dead front" display that is visible through the housing of the thermal regulator unit when illuminated, but may otherwise be invisible from the outside of the unit when not illuminated. In general the apparatus (clock display or other display) may be configured to turn off (not be illuminated) during operation, e.g., when the patient is sleeping, to prevent arousal of the user. The apparatus may include a control (e.g., button, switch, toggle, touchscreen, etc.), and the control may be configured to allow control of the illumination of the screen, display, indicators.

A thermal system for enhancing a subject's sleep may include: a thermal regulator unit having a housing, the thermal regulator unit configured to control the temperature of a thermal transfer fluid; a clock coupled with the thermal regulator unit; a display coupled with clock and the thermal regulator unit; a user input configured to allow the user to select a wakeup time; a thermal applicator configured to be worn against a subject's forehead over the subject's prefrontal and frontal cortex, wherein the thermal applicator is configured to pass thermal transfer fluid from the thermal regulator unit; a controller within the thermal regulator unit configured to regulate the temperature of the thermal transfer fluid based on one or more thermal control profiles to modulate the subject's sleep by controlling a temperature of the thermal applicator, wherein the controller is configured to modify the temperature of the thermal transfer fluid at the wakeup time; and a headgear to maintain the thermal applicator in contact with the region of the subject's head over the prefrontal and frontal cortex. The thermal applicator may be adapted to thermally regulate only the region of the subject's head over the prefrontal and frontal cortex, but not other regions of the subject's head and face including the eye orbits.

A thermal system for enhancing a subject's sleep may include: a thermal regulator unit having a housing, the thermal regulator unit configured to control the temperature of a thermal transfer fluid; a thermal electric module within the thermal regulator unit configured to heat, cool, or heat and cool the thermal transfer fluid; a first reservoir of thermal transfer fluid within an internal plumbing of the thermal regulator, wherein the first reservoir is configured to be thermally regulated by the thermal electric module; a second reservoir of thermal transfer fluid that is not thermally regulated by the thermal electric module; a valve configured to transfer fluid between the first reservoir and the second reservoir to maintain a level of thermal transfer fluid within the first reservoir; a thermal applicator configured to be worn against a subject's forehead over the subject's prefrontal and frontal cortex, wherein the thermal applicator is configured to pass thermal transfer fluid from the thermal regulator unit; a controller within the thermal regulator unit configured to regulate the temperature of the thermal transfer fluid based on one or more thermal control profiles to modulate the subject's sleep by controlling a temperature of the thermal applicator, wherein the controller is configured to modify the temperature of the thermal transfer fluid at the wakeup time to wake the subject; and a headgear to maintain the thermal applicator in contact with the region of the subject's head over the prefrontal and frontal cortex.

In some variations, the systems described herein consist of thermal regulator unit, a thermal applicator/hose assembly (sometimes referred to as the forehead pad) and a headgear to maintain the thermal applicator in contact and in position with the frontal cortex. Any of the apparatuses described herein may be used by a sleeping subject, and thus may be adapted for comfort as well as safety and efficacy. For example, the systems described herein may be configured to prevent fluid loss/leakage.

BRIEF DESCRIPTION OF THE DRAWINGS

FIG. 2A shows an exploded view of the connector and FIG. 2B shows the assembled valve without a cartridge attached.

In FIG. 3A, the cooling pad is segmented to allow conformability in both the horizontal (x) and vertical (y) direction. Additionally, the pad may allow for movement in the (z) direction to adjust for varying heights of the forehead.

Figure 3A:
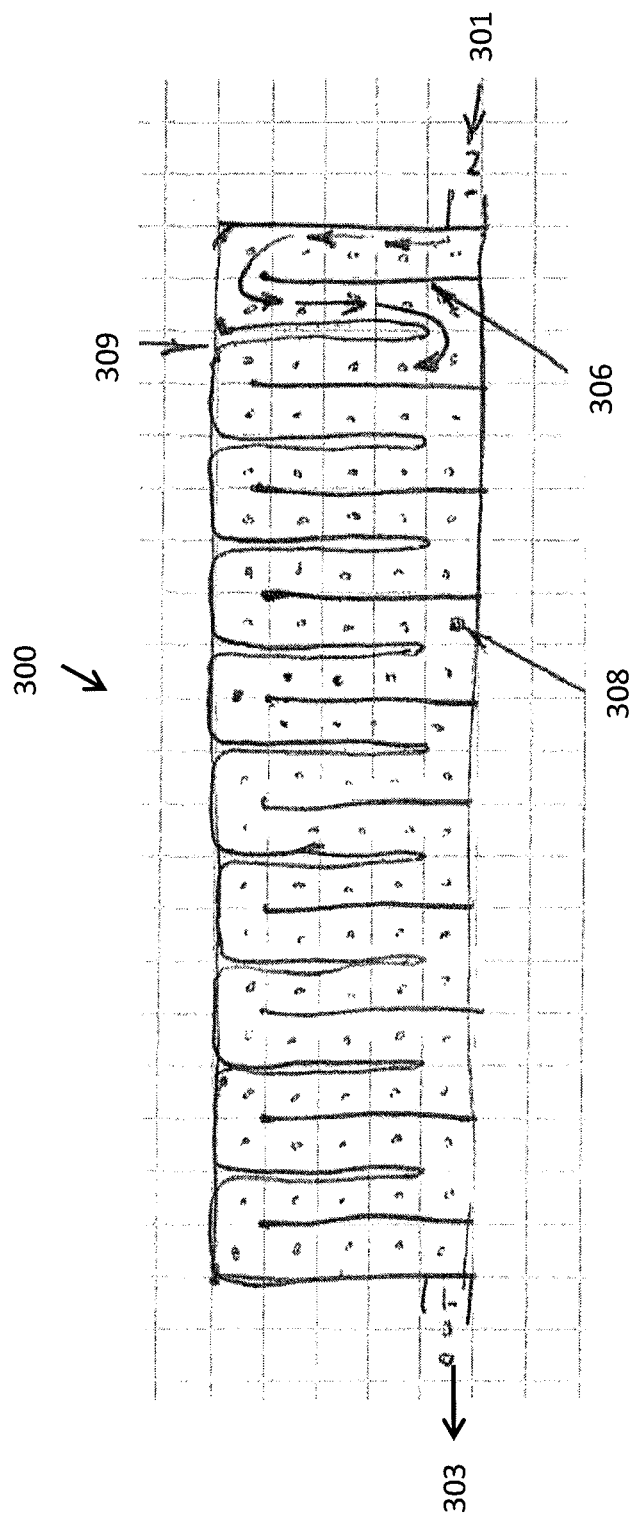
FIGS. 3A and 3B show embodiments of thermal applicators (e.g., configured as forehead pads) for thermally regulating the temperature of the frontal cortex of the brain by maximize the thermal transfer surface area while maintaining a minimal contact area on the head for optimizing patient comfort. The applicator may provide a conformable cooling path that allows the device to conform to the forehead, adapting to variations on forehead geometry and surface area.
Figure 3B:
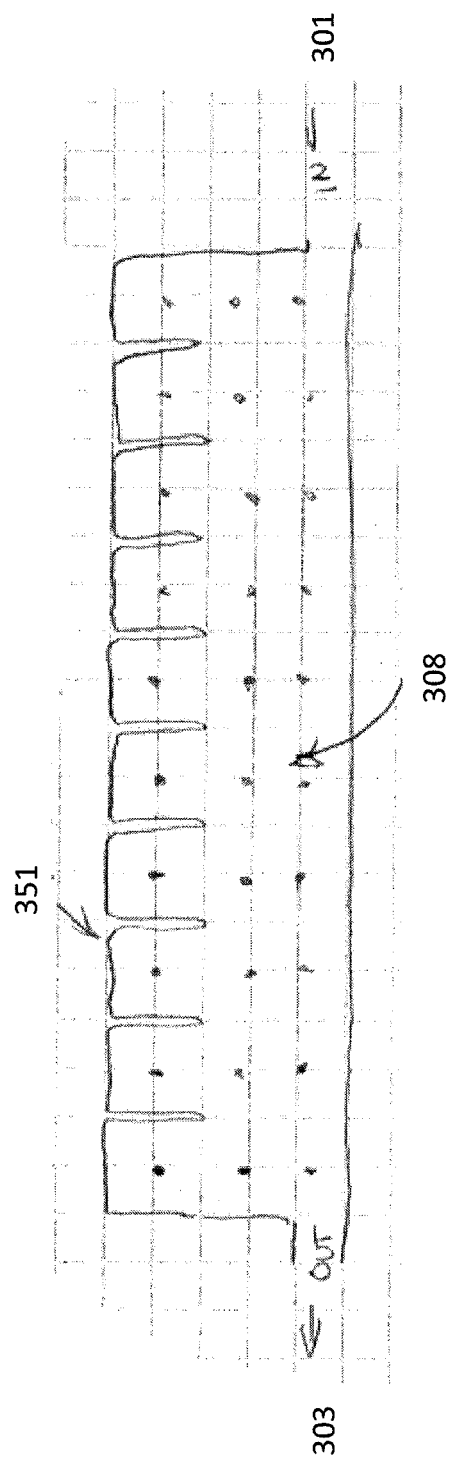

The embodiments shown in FIGS. 3A and 3B each provide an optimized flow path and surface area as well as fingers that provide conformability to the forehead.

Figure 4:
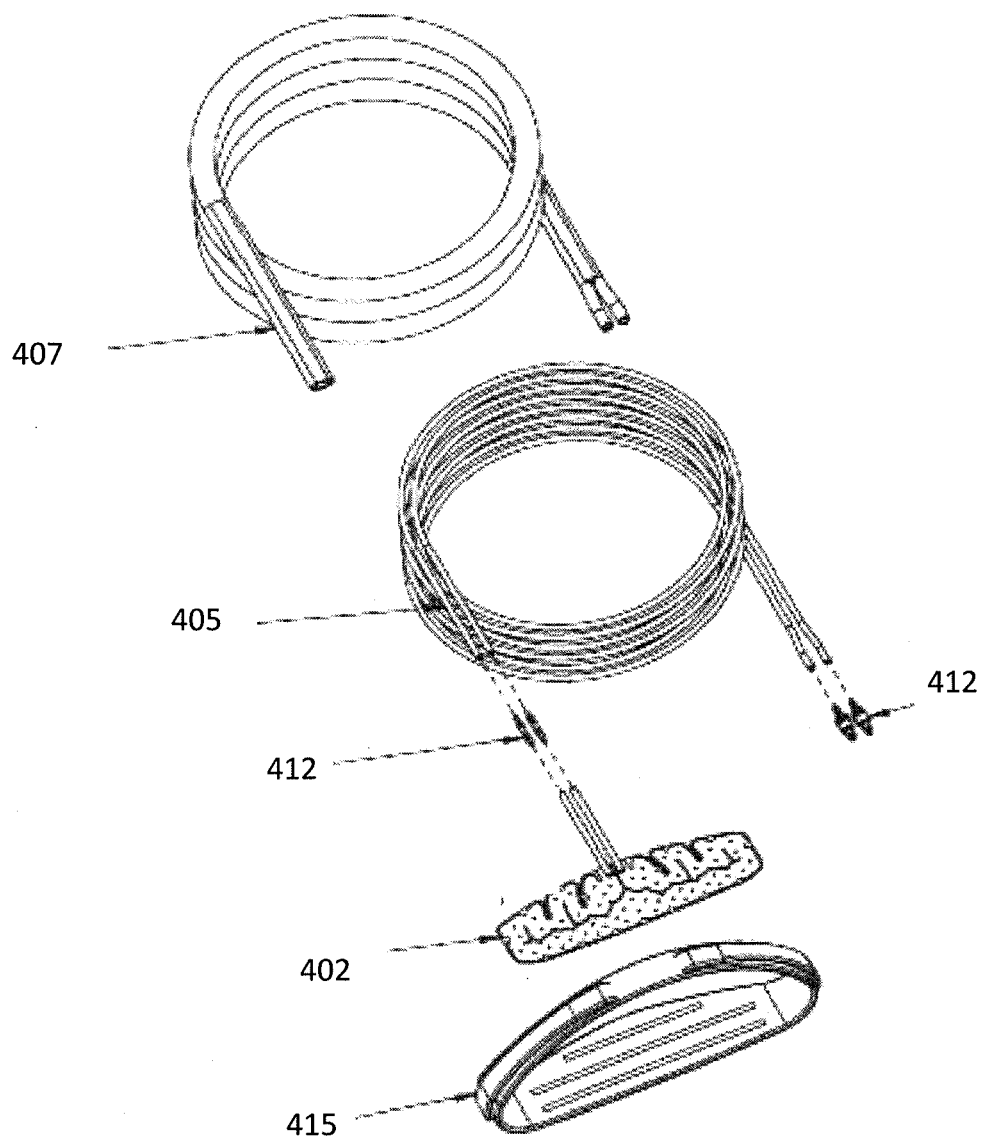

FIG. 4 shows one embodiment of the thermal applicator/hose assembly and headgear as described herein.

Figure 5:
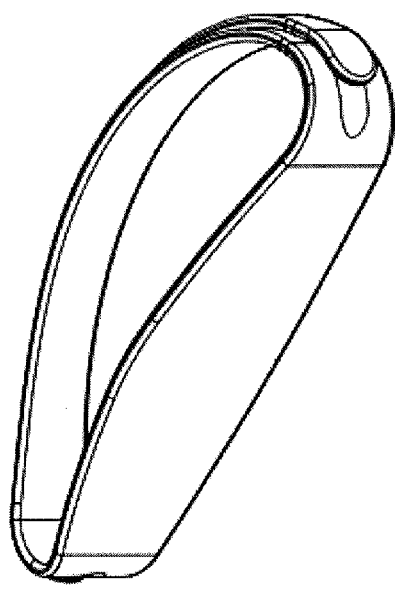

FIG. 5 depicts one embodiment of a headgear.

FIGS. 6A-6J illustrate one method of applying a system for enhancing sleep as described herein.

Figure 7A:
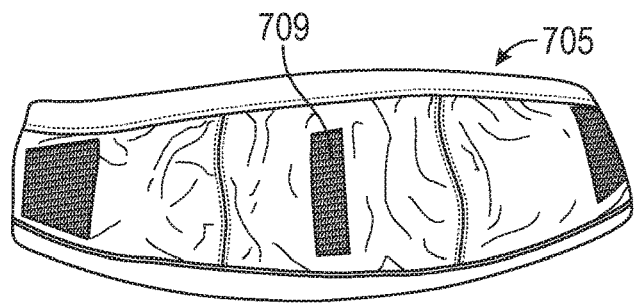

FIG. 7A shows another variation of a headgear for holding a thermal applicator.

Figure 7B:
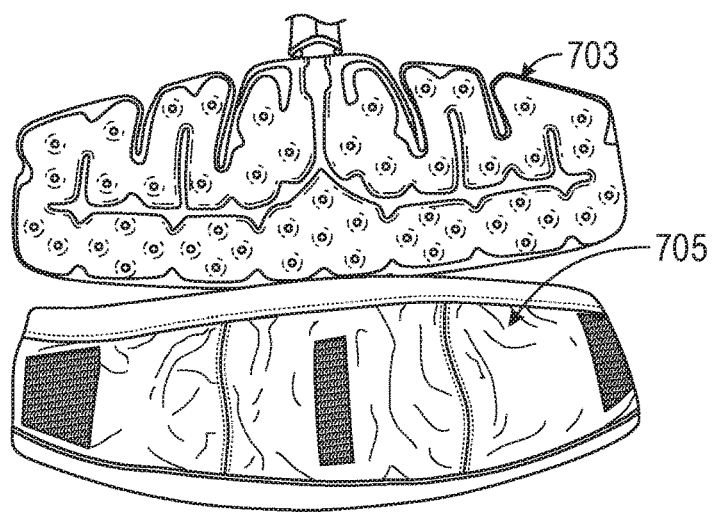
Figure 7C:
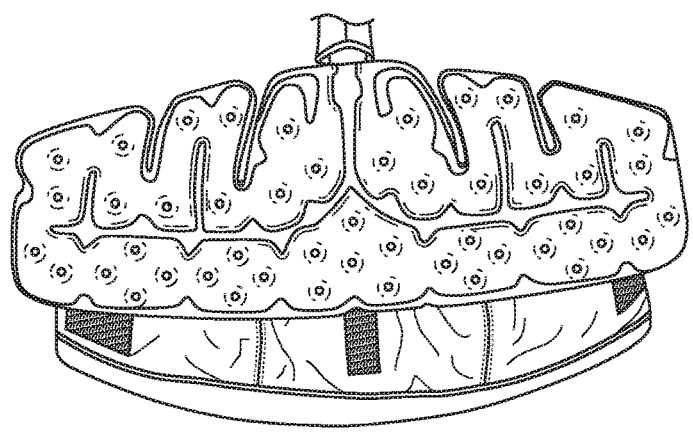

FIGS. 7B and 7C illustrate a method of inserting a thermal applicator into the headgear of FIG. 7A.

Figure 8A:
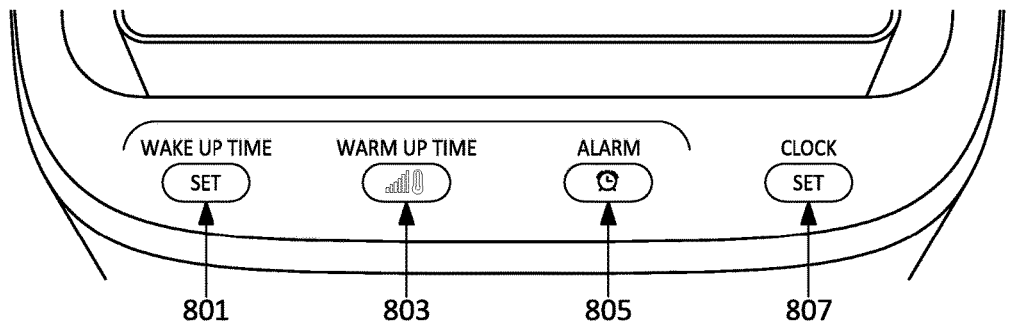
Figure 8B:
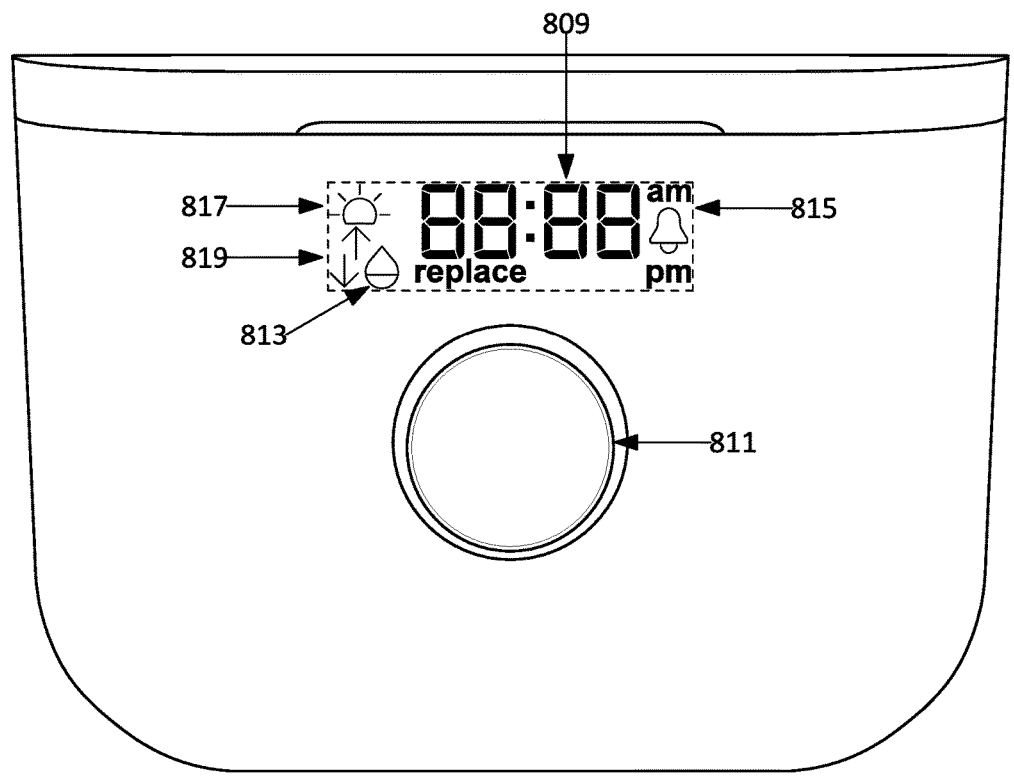

FIGS. 8A and 8B illustrate displays and controls that may be present on a thermal regulator unit.

DETAILED DESCRIPTION

Apparatuses for enhancing a subject's sleep are described, including systems for enhancing a subject's sleep that include a thermal regulator unit for controlling the temperature of a thermal transfer fluid, a thermal applicator adapted to exchange thermal energy (from the thermal transfer fluid) with a localized region of the subject's head (e.g., the region over the prefrontal/frontal cortex) and a controller configured to control the thermal regulator and therefore the exchange of thermal energy with the localized region of the subject's head. Any of the apparatuses described herein, which may include devices and systems, may be adapted to include a refillable and/or removable cartridge (e.g., reservoir) of thermal transfer fluid that is not thermally regulated, while an internal pool of thermal transfer fluid (e.g., within the internal plumbing of the thermal regulator unit) is regulated. Any of these apparatuses may also include a clock coupled to the controller, and the controller may be configured to allow a subject to select, e.g., from a menu of profiles, the thermal control profile to apply to modulate sleep. Any of these apparatuses may be adapted to allow the subject to select a wakeup time; the wakeup time may trigger an alarm, and/or prior to the wakeup time the apparatus may transition the temperature of the thermal transfer fluid, and thus the applicator, to a predetermined wakeup temperature (e.g., ambient temperature, some offset of ambient temp, etc. which may enhance the subject's comfort and clarity upon waking up and/or may assist in waking the patient.

Exemplary system configurations and methods of operation to enhance sleep are provided herein.

In general, these systems may include a thermal regulator unit, a thermal applicator, a conduit for transferring thermal transfer fluid between the thermal regulator unit and the applicator (e.g., a hose assembly) and a controller. The apparatus may also include a headgear to maintain the thermal applicator in contact and in position with the region of the subject's head over the frontal cortex. As mentioned above, a systems described herein may be worn by a sleeping subject, and thus may be adapted for comfort as well as safety and efficacy. The systems described herein may be configured to prevent fluid loss/leakage.

The thermal regulator unit may be at least partially enclosed in a housing, and may include one or more displays, controls, and connectors. For example, a display may be visible on the device and may display control information, time (e.g., clock), temperature, on/off status, etc. The display may be adjustable and/or timed so that it is not constantly illuminated during operation, so as to disturbing a sleeping subject, or a subject attempting to fall to sleep. In some variation the display is a "dead-front" display that is only visible when illuminated.

The apparatus may also include a clock (e.g., within the housing); the clock may form a part of the controller. In general, the controller is configured to control the thermal regulation of the applicator, e.g., by controlling the temperature of the thermal transfer fluid and/or the circulation of the thermal transfer fluid to/from the applicator. The thermal regulator unit generally drives/controls a single applicator, however it may be configured to control (separately or collectively) multiple applicators.

The controller may be any appropriate controller, including a microcomputer controller (dedicated or general-purpose). The controller may store information (e.g., control profiles) and may allow a subject to select which profile to apply as well as the timing (e.g., on-time, wakeup/off time, etc.). In some variation the controller may also record information on the operation of the device and/or the sleep status of the subject. This information may be stored, displayed, and/or transmitted; thus, in some variations the controller includes or is coupled to an output such as a wireless transmitter (e.g., Bluetooth, etc.).

Figure 1A:
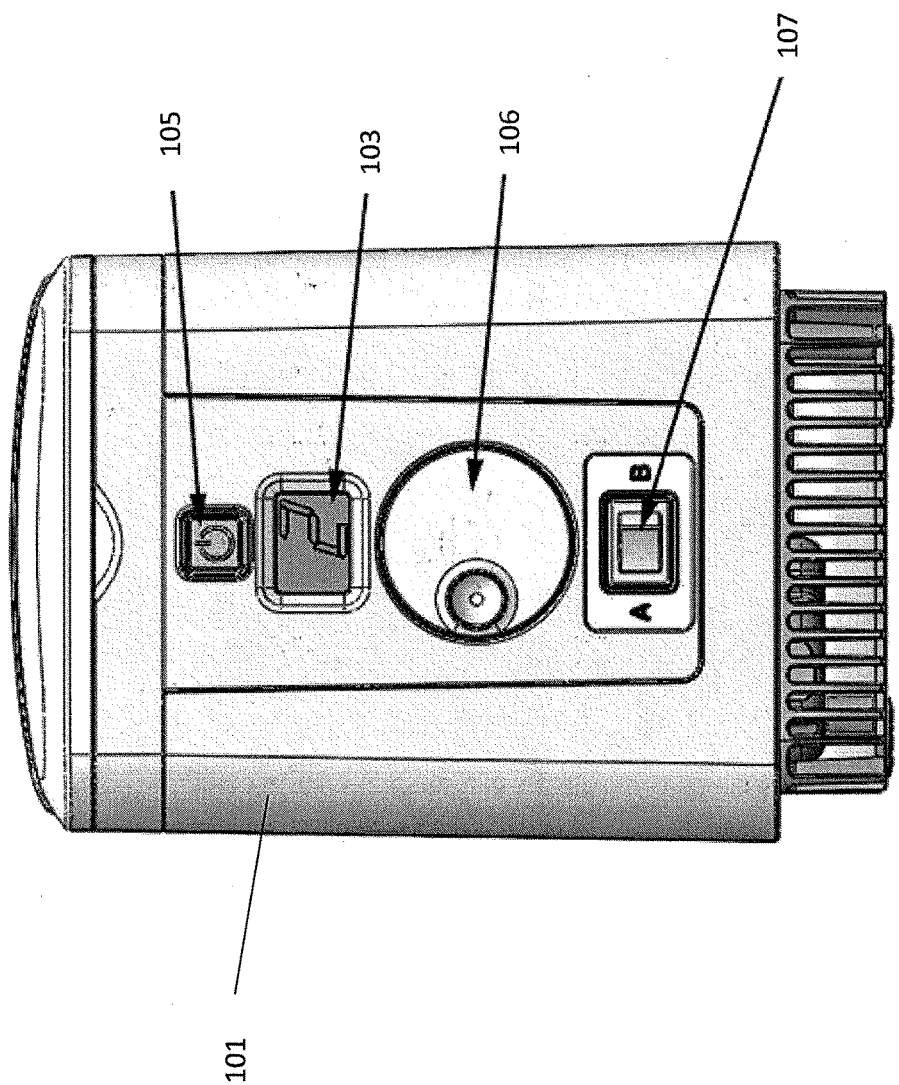
FIG. 1A is a front view of one variation of a thermal regulator unit of an apparatus for enhancing a subject's sleep.

For example, FIGS. 1A-1J illustrate one variation of a thermal regulator unit that may be used with an applicator to enhance a subject's sleep. In FIG. 1A, the thermal regulator unit includes an outer housing 101, as well as a display (e.g., temperature/profile selection and/or time display) 103, and one more controls. For example, the apparatus may include a power switch and/or indicator 105, a selector knob 106 (e.g., for selecting the temperature/profile), and/or a toggle for switching profiles 107 (e.g., between a cooling/heating configuration, etc.). FIGS. 8A and 8B illustrate other examples of inputs and indicators that may be used on a thermal regulator unit. For example, in FIG. 8A, the thermal regulator may include an input allowing a user to set the desired wake up time 801 (e.g., the time that an alarm will sound, and/or ½ hour before TEC's shut off). The unit may also include a control (button, switch, etc.) for enabling or disabling a warm up mode 803. As described in detail below, the warm up mode may allow the apparatus to ramp to a temperature for waking up prior to the selected wake-up time (e.g., approximately ½ hour before wake up time). A control may also be provided for enabling/disabling an alarm tone 805 (set by an alarm clock), and for setting the internal alarm clock 807.

FIG. 8B shows an example of a display that may be included on the thermal regulator unit. As mentioned, the display may be configured as a dead front display. In FIG. 8B, the display 809 may show the time of day, alarm time, temperature profile, and any other status indicator for the apparatus. The thermal regulator unit may also include a control (such as control knob 811) for selecting/adjusting temperature profile, alarm time, display intensity and clock time. For example, the control knob may be pressed and held to toggle the unit from a therapy mode to a standby mode. The display may also include a level indicator 813 configured to indicate that fluid level in the apparatus is running low. An alarm icon 815 may also be shown, and may indicate that the alarm tone is enabled. The display may also include a warm-up icon 817, indicating that the warm-up mode is enabled. Directional arrows 819 on the display may also be illuminated to indicate the direction of rotation of the knob/control 811.

Figure 1B:
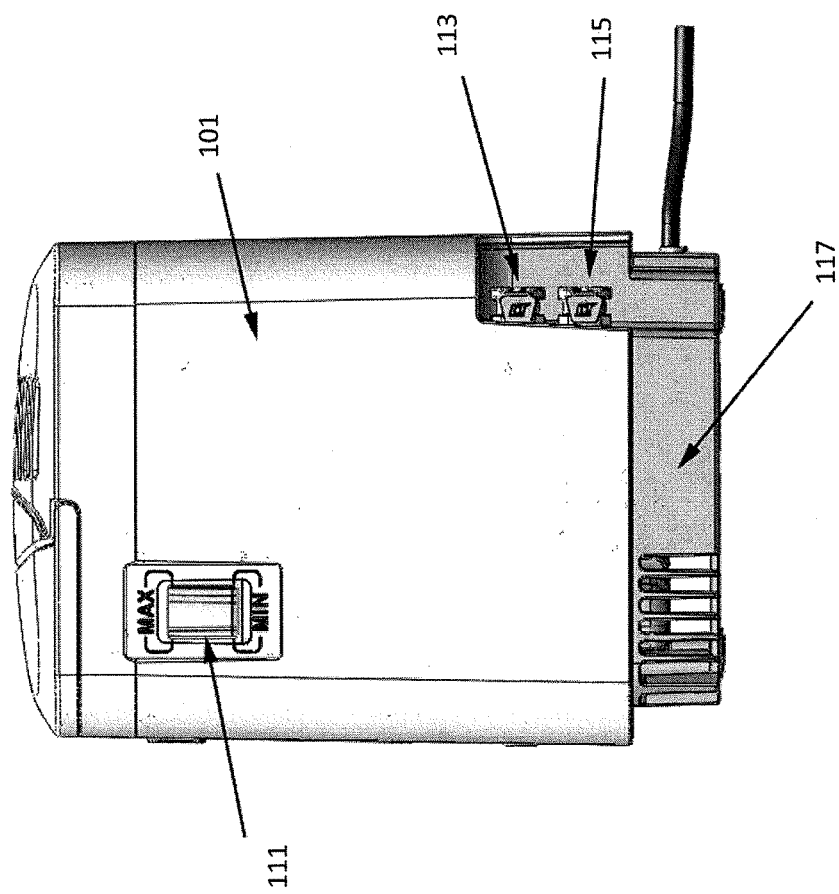
FIG. 1B shows side views of the apparatus of the thermal regulator unit shown in FIG. 1A.
Figure 1C:
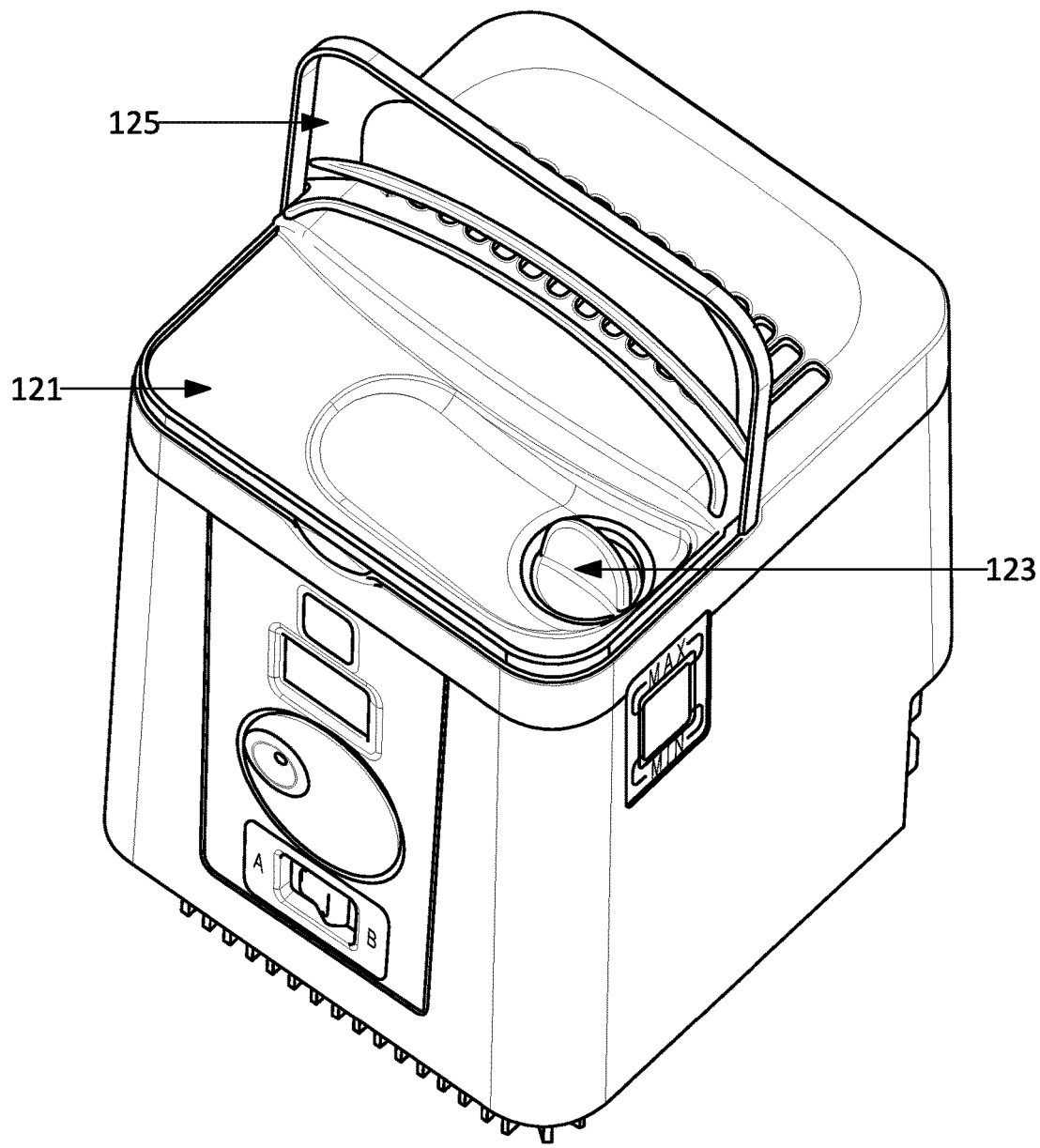
FIG. 1C shows a top perspective view of the front.
Figure 1D:
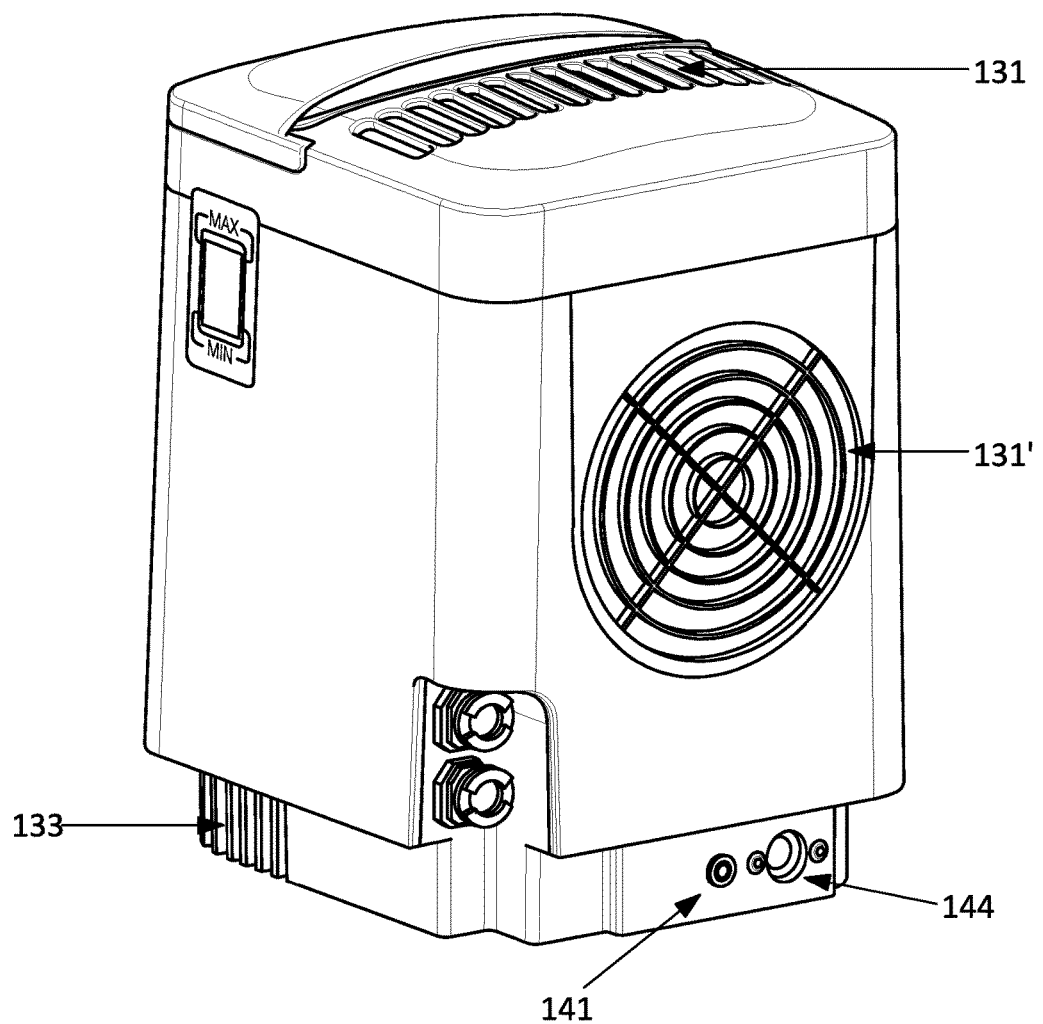
FIG. 1D shows a top perspective view of the back of the thermal regulator unit of FIG. 1A.
Figure 1E:
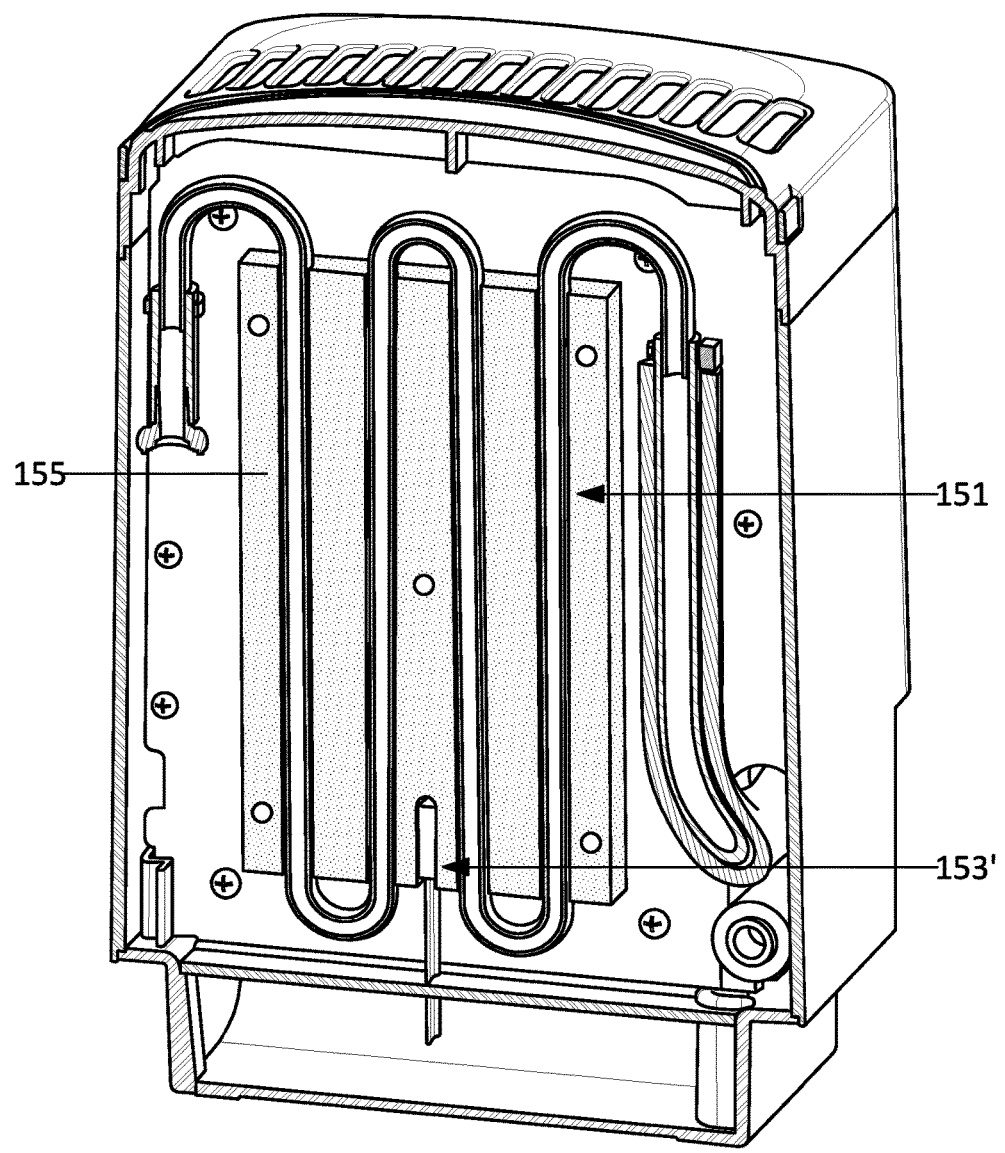
FIG. 1E shows a section through the thermal regulator unit of FIG. 1A.

Returning now to FIG. 1A, FIG. 1A shows a front view, while FIG. 1B shows a side view of one variation of a thermal regulator unit. In FIG. 1B, the unit includes a fluid level indicator (window 111), as well as a sealing connection to the conduit(s) connecting to the applicator, through which the thermal transfer fluid may be circulated; in FIG. 1B, these sealing connections are shown as a fluid inlet port 113 and a fluid outlet port 115. The housing may also include a base 117. FIG. 1C shows a view of an upper region of the thermal regulator unit of FIG. 1A; the top of the apparatus may include a lid 121 and a fill cap 123. Thermal transfer fluid may be applied or withdrawn through the sealable fill cap 123. The lid may also include a door or cover 125 for covering the fill cap region. The housing 101 may include vents 131, 131' as shown in FIG. 1D. In FIG. 1D the vents are configured as fan inlet vents 131 and fan outlet vents 131'. The housing (e.g., the base portion) may also include additional vents (e.g., fan outlet vents 133) and/or output ports 141, power connections 144, or the like.

FIGS. 1E to 1I show internal regions of the thermal regulator unit of FIG. 1A, including a temperature regulator (e.g. fan, heater, etc.), the internal plumbing holding the thermal transfer fluid, one or more pumps for circulating the thermal transfer fluid, and the controller.

In general, a thermal regulator unit may include one or more temperature regulators for regulating the temperature of the thermal transfer fluid to be circulated to the applicator. Any appropriate temperature regulator (e.g., heater, cooler, or both) may be used. For example, a thermal regulator unit may utilize thermal electric modules (TECs), e.g. Peltier devices, to cool or heat a thermal transfer fluid (TTF) which is pumped through transfer lines of the thermal applicator. Other cooling or heating means such as a refrigeration compressor could also be used instead or in addition to TECs. For example, resistive heaters, fans, or other elements may also or alternatively be used. Other components of the thermal regulator unit may include a one or more heat exchangers, heat sinks, TECs, a pump, fan, electronic control circuits, software, user interface, TTF reservoir, unit enclosure, connections for incoming electrical power, and TTF connections for the thermal applicator.

The components may be assembled such that the heat sink(s) are placed in thermal contact with one side of the TEC(s) and the heat exchanger (sometimes referred to as a cold plate) is placed in thermal contact with the opposite side of the TEC(s) away from the heat sink. The heat exchanger can be constructed from any known material and design for the purpose. One example of which is a copper tube imbedded within an aluminum plate. A fan may be used to remove heat from the heat sink. Portions of the assembly can be insulated to reduce parasitic heat loads on the heat exchanger.

Returning to FIG. 1E, the thermal regulator unit of FIG. 1A includes a cold plate (aluminum plate 155 with copper tubing 151), a TEC (not visible, e.g., one or more Peltier device), and a thermal protector 153 for monitoring the temperature of the system, which may be present on either or both the cold side and the hot side. The tubing 151 forms part of the internal plumbing holding the thermal transfer fluid. The thermal protector may include a sensor (e.g., a thermal cutoff) that monitors the temperature and can limit the temperature of the device and trigger an automatic shutdown of the system.

The thermal regulator unit in FIG. 1A can be operated in a warming or cooling mode to control the temperature of the TTF to the desired levels. The thermal regulator may utilize a pump to circulate the TTF through the heat exchanger and the thermal applicator. The pump can be of any appropriate type, i.e. centrifugal, piston, gear, diaphragm etc. A TTF reservoir is incorporated to provide additional TTF to replenish the TTF lost for any reason. For example, the reservoir may be configured as a cartridge that is removable (or not removable) from the thermal regulator unit. Thus, a reservoir can be an integral fillable component within the thermal regulator unit or can be constructed as a replaceable cartridge. The plumbing connection for the reservoir may be designed such that the volume of the TTF within the reservoir is not serially located within the TTF circulation circuit of the heat exchanger and the thermal applicator. This design is referred to as a side stream reservoir.

Figure 1F:
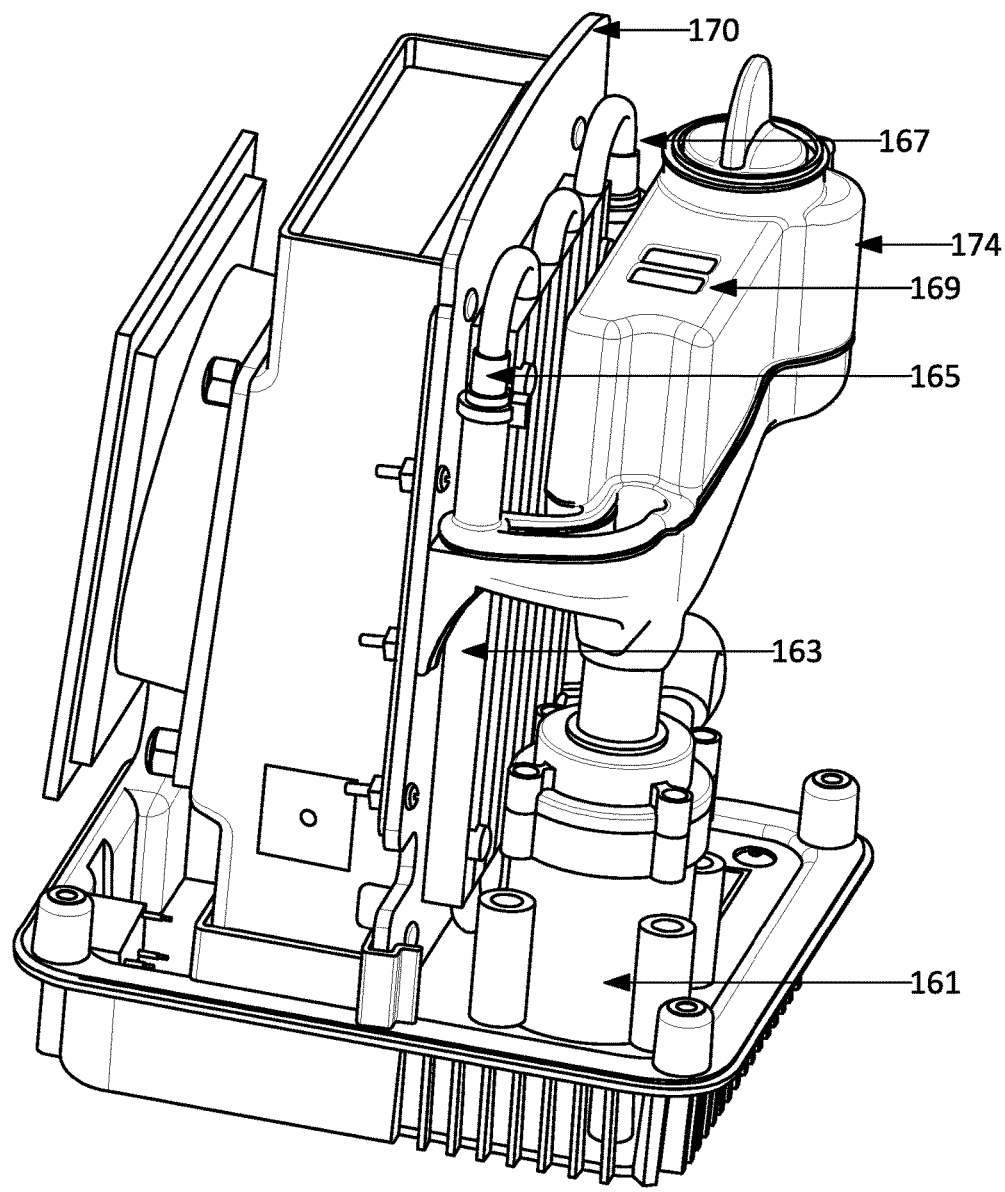
FIGS. 1F and 1G shows side perspective views of the thermal regulator unit of FIG. 1A with the outer cover removed.
Figure 1G:
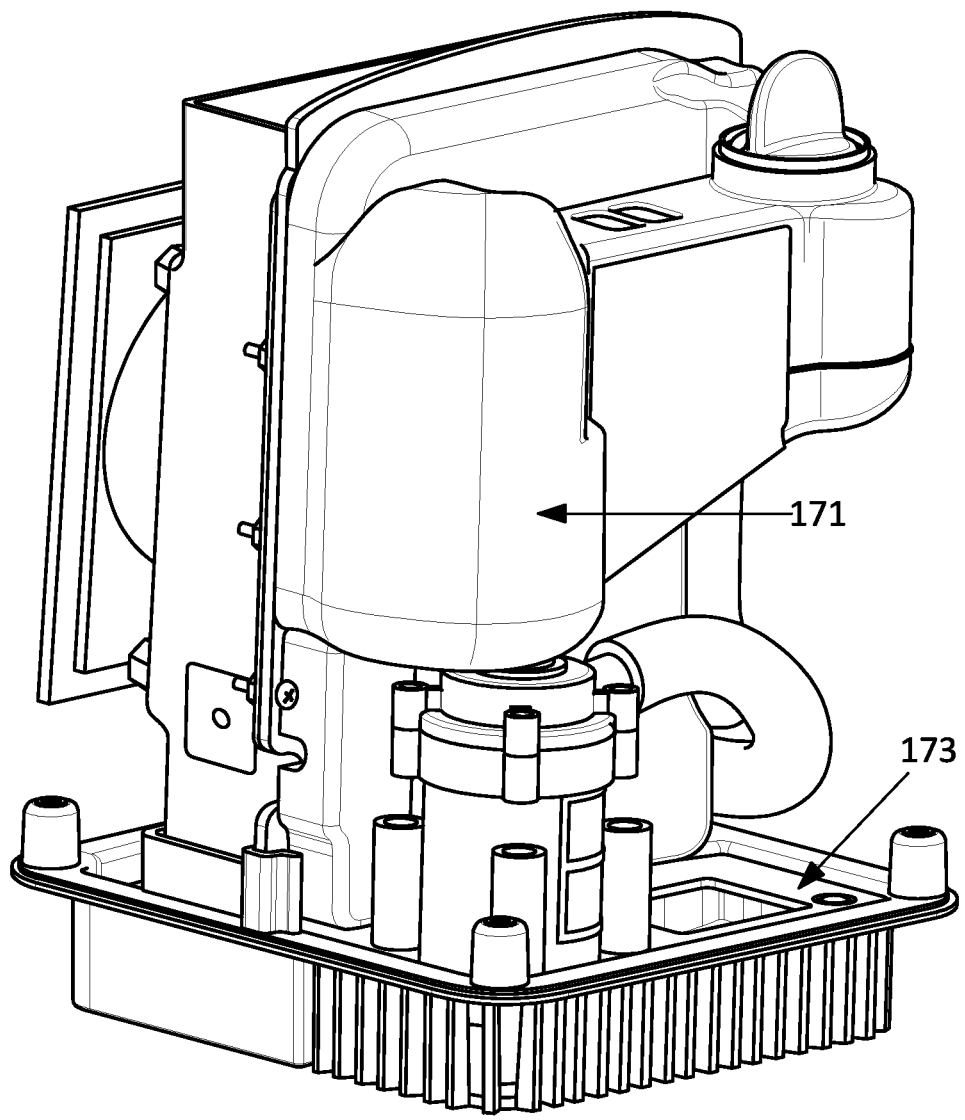
Figure 1H:
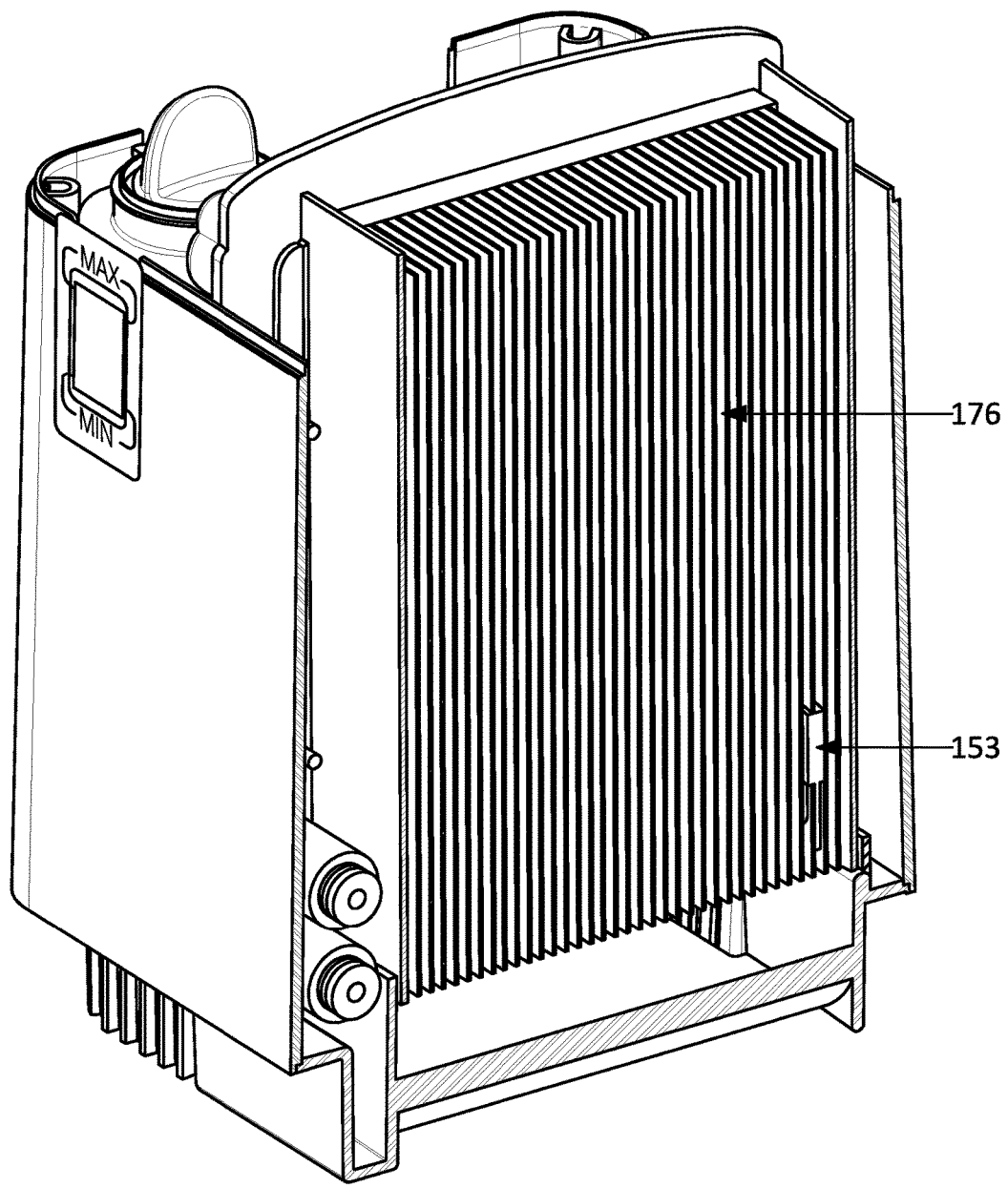
FIG. 1H is a view of the thermal regulator unit of FIG. 1 with the front and top removed to reveal internal structures.

FIG. 1F is another view of the thermal regulator example of FIG. 1A, showing a pump 161 for circulating thermal transfer fluid, as well as a heat sink, cold plate 163, and a pair of thermistors 165, 167. The temperature of the thermal transfer fluid may be monitored (e.g., by the controller) to regulate according to the control profile selected; for example a thermistor may measure the temperature of the TTF at various locations, including a thermistor near the fluid output 165 and the fluid input 167 of the internal plumbing in the region where the thermal control unit regulates the temperature of the TTF. As shown in FIG. 1G, the internal plumbing of the thermal regulator (holding the pool of TTF that is being thermally regulated) may be insulated 171 within the housing of the thermal regulator unit. Venting 173 may also be included for internal cooling/heating components, such as fans. Returning to FIG. 1F, a barrier 170 separates the cold side of the device from the hot side of the device, and may form part of the housing for one or more TEC (not visible in FIG. 1F). In FIG. 1F a reservoir 174 for TTF is also shown. The reservoir may hold TTF that is not typically temperature controlled. TTF from within the reservoir can be added to the internal plumbing of the thermal regulator as needed. This reservoir may be fixed in the housing of the thermal regulator, or it may be removable/replaceable. For example, the reservoir may be configured as a cartridge, e.g., a removable cartridge, and may include a vent 169; the vent may allow air into the reservoir (allowing fluid to go into the internal circuit of the thermal regulator unit), and may allow purging of air from the internal plumbing of the thermal regulator unit. For example, in FIG. 1F, the vent may be Gore-Tex™ or another material that is air-permeable but not fluid-permeable.

Figure 1I:
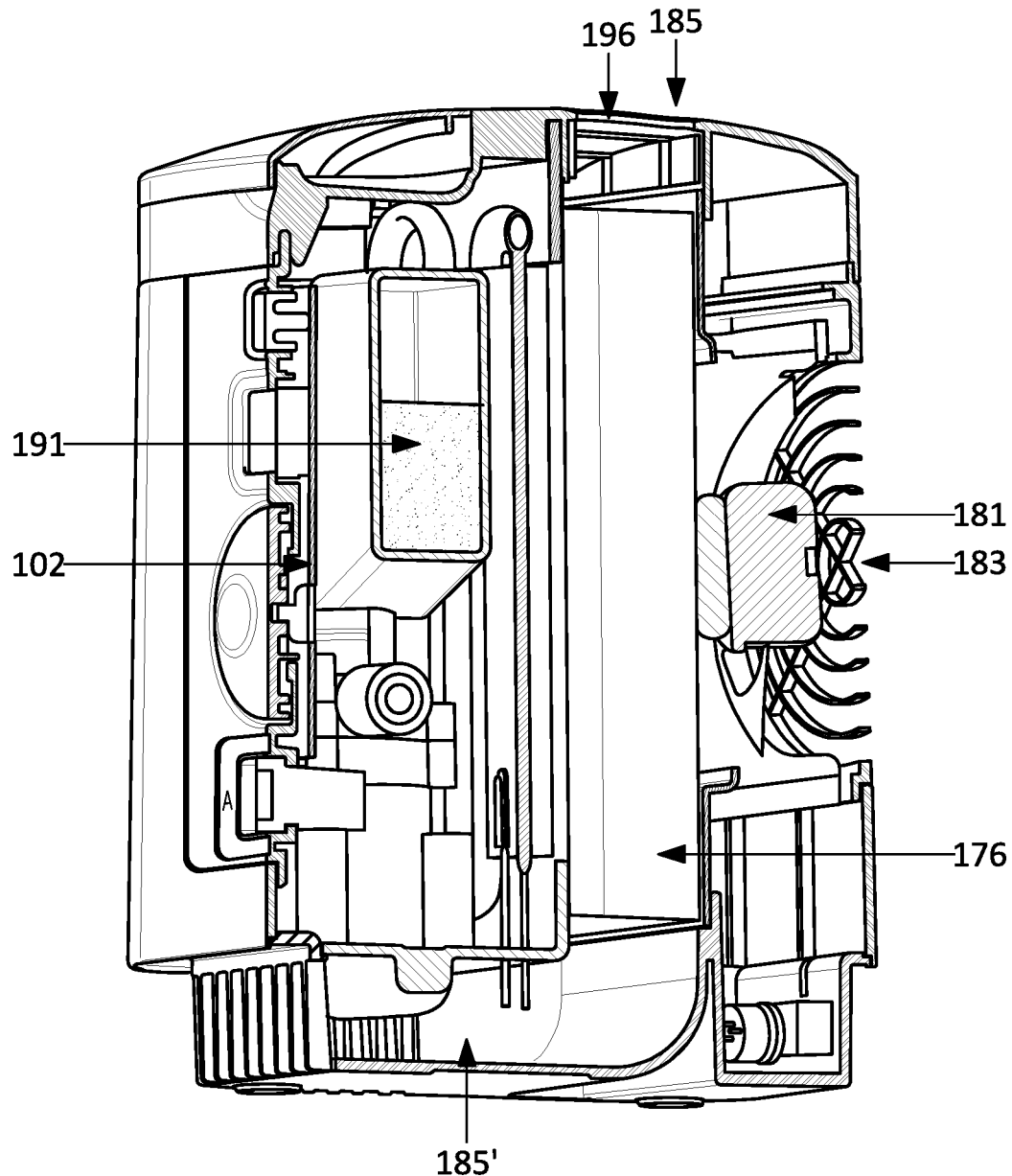
FIG. 1I shows another side section though the thermal regulator unit of FIG. 1A.

FIG. 1I show a section through the thermal regulator unit, showing the relative positions of the heat sink 176, fan 181, fan air inlet 183, fan air outlets 185, 185', and housing 101 for the variation shown in FIG. 1A. The thermal regulator unit may also include a control panel 102 on the housing 101 as mentioned above. In FIG. 1I, thermal transfer fluid 191 is shown within a reservoir of the internal plumbing of the thermal regulator unit.

FIGS. 1A-1I illustrate an apparatus having a reservoir (e.g., cartridge) of TTF that is not thermally regulated until it is needed. This side stream configuration effectively allows the thermal regulator to cool the circulating TTF to the desired temperature faster by eliminating the need to cool the TTF held in the reservoir. The reservoir or replaceable cartridge can be sized as required to provide the desired capacity for the user's convenience. The replaceable cartridge can be configured with a valve system that allows the user to engage or remove the cartridge into the thermal regulator without causing a leak of TTF. The cartridge may be configured with a one way vent to allow air intake as the TTF is drained from the cartridge. This configuration allows the TTF to drain from the cartridge and not re-enter the cartridge if a back pressure is generated within the circulating circuit. If this type of one way vent is utilized in the cartridge, a separate air vent may be plumbed into the circulation circuit to allow air trapped within the circuit to exit. Another configuration of the cartridge utilizes two connection points into the thermal regulator. One connection allows air trapped within the circulation circuit to vent into the cartridge while TTF is allowed to drain into the circulation circuit from the second connection point. The connection valves may be designed in any number of known configurations. One such implementation utilizes check valves in each of the mating connection components. This may provide a means of engaging or removing the cartridge without TTF leaking from the removed cartridge or from the mating connection point within the thermal regulator. In another variation the cartridge is sealed with a rubber type material that can be punctured with a hollow needle. Once punctured the TTF would make a fluid connection with the circulation circuit. When the cartridge is removed, the needle would be withdrawn allowing the rubber type material to reseal the puncture hole preventing the TTF from leaking from the cartridge. The needle would be designed with a spring loaded sliding rubber type material seal that would slide over the inlet port on of the needle when the cartridge is removed (e.g., FIGS. 1A-1I and FIGS. 2A-2B). Another variation utilizes ball type or O-ring seal type check valves commonly known. The cartridge size and shape are determined by the required capacity, the desired cosmetic industrial design and the available space within the enclosure. Once engaged in the thermal regulator, the cartridge is held in place by any latching mechanism. In another embodiment, the cartridge air vent is bi-directional and may be constructed of a material such as Gore-Tex. Such a material allows air to pass through it while preventing TTF from passing. As mentioned above, in some variations a cartridge may include a fluid reservoir held within a collapsible bag; as fluid is withdrawn from the bag (or bladder) the bag may collapse, reducing or eliminating the need for venting of the reservoir.

The cartridge and engagement valves are designed to prevent or minimize the potential of the user refilling the cartridge. This design will ensure the user only utilizes TTF specifically formulated for the cooling unit.

Figure 2A:
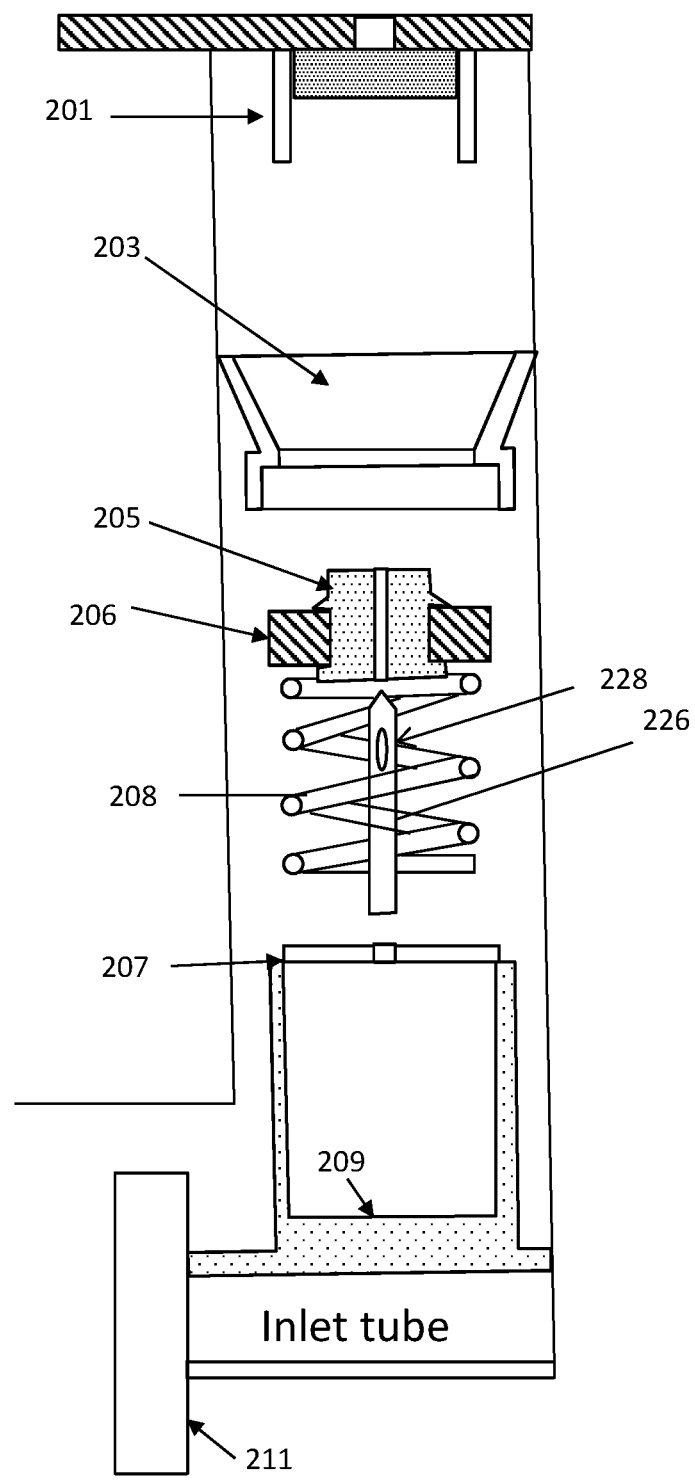
FIGS. 2A and 2B depict one variation of a valve/connector for a cartridge (e.g., reservoir).
Figure 2B:
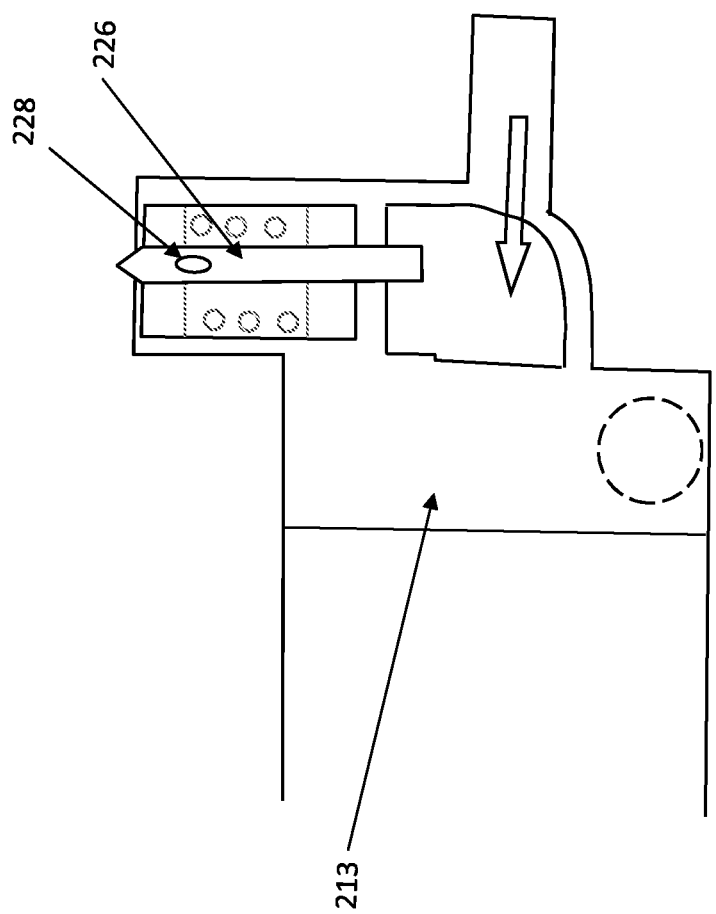

FIGS. 2A and 2B illustrate one variation of a cartridge connector (or valve) and cartridge. FIG. 2A shows an exploded view of the valve. The bottom region of the cartridge 201 is shown at the top of the figure, and includes an inlet region that is covered by a seal material that can be pierced by a needle 226 in the connector. The base of the cartridge can dock with the cartridge connector, causing the cartridge connector to engage with the cartridge, and extending the needle from a protective seal into the reservoir of the cartridge so that TTF can pass from the cartridge into the inlet of the thermal regulator unit. In FIG. 2A, the top of the connector includes a retainer cap/cartridge lead in region 203 forming a base onto which the cartridge can sit. This retainer cap is connected to a silicone slide seal 205. The retainer cap and slide seal are supported by a spring 208. When the cartridge rests on the retainer cap, the weight of the cartridge drives the retainer cap and the slide seal 205 down, collapsing the spring, so that the tip of the needle 226 can extend out of the slide seal and into the cartridge. The tip of the needle 226 is sharp, and a side portion of the needle includes an aperture 228 into which TTF from the cartridge may pass. When the cartridge is not present, the needle tip and aperture 228 are held in the sliding seal 205 preventing fluid from leaving the internal plumbing of the thermal regulator unit through the needle.

The needle may be rigidly held and sealed within a needle aperture (seal retainer) 207, and a press fit seal 209. FIG. 2B is view of the assembled cartridge connector before engaging the cartridge with the thermal regulator unit. The needle allows flow of TTF from the cartridge into the inlet tube for the pump; in FIG. 2A, the pump 213 is shown by cover plate 211.

The TTF can consist of but is not limited to distilled water, an anti-microbial agent, a component to lower the freezing point and a wetting agent. Other TTF ingredients could also be used. All TTF may be compliant with the bio compatibility requirements of IEC 60601 and FDA requirements.

The control circuits may or may not utilize software for controlling the cooling or heating of the thermal regulator unit. As mentioned, the control circuit may utilize one or more temperature sensors (e.g., thermistors) located within or in proximity to the circulating circuit to measure the temperature of the TTF and adjust the power to the TECs as required to maintain the TTF within the circulating circuit at the desired temperature. Additionally, the control circuit can utilize one or more thermal control switches located on the heat sink and possibly the heat exchanger as a safety switch in case temperatures on one or both components are outside the desired thresholds. The control circuit may utilize Pulse width modulation (PWM) to provide power to the TECs, pump and fan. Software can also be utilized to provide control algorithms for controlling all aspects of the system. The software could control the power to be supplied to the TECs in such way to produce any desired cooling curve of the TTF. In one variation the power could be applied to the TECs such that the TTF is cooled more rapidly with the onset of power and the rate of temperature change is reduced as the actual TTF temperature and targeted TTF temperature difference becomes smaller. There are other temperature curves that could be considered. Additionally, the TTF temperature could be controlled by user physiological measurements or by time. The control circuits can also provide a user interface to the cooling unit. Possible variations could include but not be limited to an on/off switch, heat/cool mode selector switch, temperature display of targeted temperature or actual temperature of the TTF. The control circuit could also control display lighting. In some variations the control circuit can monitor the level of TTF in the reservoir or cartridge and display the level to the user. The control circuit could also shut the unit off if it detected a low or empty TTF level.

The enclosure provides a means of mounting all of the internal components of the system and provides for air intake and exhaust of the fan air. The fan inlet and exhaust can be directed through a grid system within the enclosure that is designed to prevent users from coming in contact with components that could produce an injury. Furthermore, the grids may be designed in such a way to allow the user to direct the airflow in a direction they find desirable. The enclosure allows for a conveniently positioned user interface, reservoir filling or cartridge replacement, a visual means for determining the TTF level remaining, connection points for incoming power, connection points for the inlet and outlet of the circulating circuit thermal applicator/hose assembly and any other desirable connections.

The inlet/outlet connectors of the thermal applicator/hose assembly and the thermal regulator enclosure connectors utilize check valves that allow the thermal applicator/hose assembly to be connected and removed from the regulator assembly without leaking TTF from either component. The hose portion of the assembly is sufficiently insulated to prevent or minimize condensation on the hose assembly to the desired ambient temperature and humidity conditions. The thermal applicator component of the system may be designed to form a seal between at least two layers of flexible rubber like material. The seal may be formed by any known technique such at ultra-sonic welding, RF welding, adhesive bonding or chemical welding. The flexible material layers are selected from a wide range of known materials that exhibit the desired material properties such as flexibility, conformability, permeability, comfortable feel for the user etc. such as urethane or vinyl sheet. It is desirable the material is bio-compatible. The seal formed between the layers forms a flow channel or passageway for the TTF to circulate while the applicator is in contact with the user's skin. The thermal applicator acts as a heat exchanger when used in this way. The TTF which is temperature controlled by the thermal regulator is pumped through the hose portion of the assembly into the thermal applicator in contact with the user's skin. Thermal energy is transferred to or from the user depending upon the selected temperature of the TTF and the user's skin temperature. The design of the channels and the total length of channels produced by forming the seal between the layers of the applicator effect the amount of energy transferred. The design of the channels and the circulation path within the applicator also effect the temperature variation within the applicator. It is desirable to design the channels in such a way to maintain an even distribution of temperature across the applicator. The inlet and outlet connections of the hose to the thermal applicator may be made permanent or utilize the type of connections that can be disconnected. The design of the channels within the applicator may vary in size or cross sectional area to produce desired pressures, temperatures or flows within the channels. Additionally, the use of small weld spots or dots within the flow channels may be used to control ballooning of the channel while under pressure. The outer perimeter of the applicator is designed to provide contouring of the applicator to the desired portion of the user's skull in proximity to the fontal/prefrontal cortex. This area is generally defined as the area including the left and right temple area and the area defined between the eyebrows and the top center of the head. The applicator perimeter may also include a variety of cuts, slits or other geometrical definitions that allow the applicator to better contour to the user's head within the desired contact area. FIG. 2 shows variations of the applicator and depicts the aspects of the design discussed.

FIGS. 3A and 3B illustrate sections though thermal applicators that may be used. FIGS. 7A-7C also illustrate one variation of a thermal applicator. In FIG. 3A, the applicator (shown as a top down view, with internal structures visible) includes an inlet 301 and an outlet 303 that connect to serpentine channels within the applicator 300. The applicator in FIG. 3A has a variety of "cuts" 309 or spaces formed between adjacent channels for the TTF within the applicator; these channels may allow the applicator to be bent or form-fitted over the subject wearing the applicator. The applicator may be sized, shaped and/or pre-contoured to conform to the appropriate region of a subject's head over the frontal/prefrontal region (e.g., forehead). The applicator may be formed of a material that can be sealed or otherwise shaped to form the internal channels 306, 308. FIG. 3B shows another variation of an applicator having "finger" regions 351 that may also assist with adjustability of the applicator. In FIG. 3B the region within the applicator may be relatively open 351, allowing mixing of the TTF within the applicator.

FIG. 4 illustrates one variation of a conduit (e.g., tubing) that may be used to connect the thermal applicator 402 (which can be held within a headgear 415 to the thermal regulator unit so that thermal transfer fluid can be circulated within the applicator. In FIG. 4, the tubing 405 is covered by a thermal insulator 407; connectors 412 connect both the inlet and outlet lines. The inlet and outlet lines are joined and insulated by the same insulator, although they may be separately insulated within the insulator 407. FIG. 5 shows an enlarged view of the headgear.

When a headgear is used with the apparatus, the applicator may be positioned within the headgear, as illustrated in FIGS. 7A-7C. For example, in some variations the applicator (pad) 703 is configured to disconnect from the headgear 705. The headgear may include a connector to couple with the applicator, such as Velcro or the like. In some variations, the headgear includes a pocket into which the applicator may sit. In FIG. 7A, the headgear is shown inside out, with interior Velcro inserts 709 showing. The applicator may fit into the headgear and the headgear may include a thermally transmissive region that permits the transfer of thermal energy between the applicator and the subject's head in the correct regions (e.g. forehead).

Figure 6A:
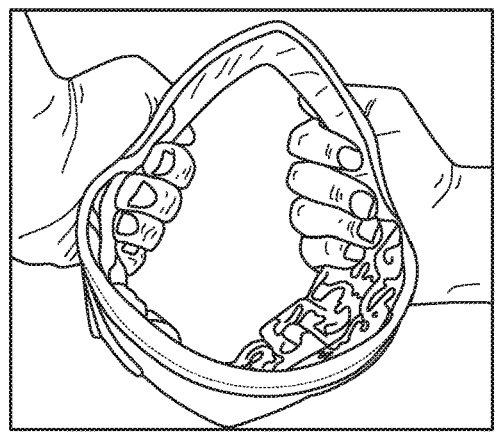
Figure 6B:
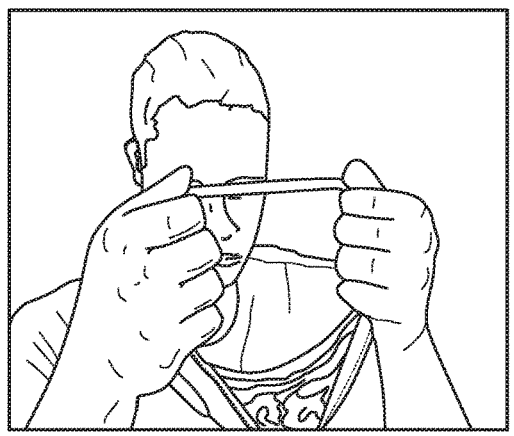
Figure 6C:
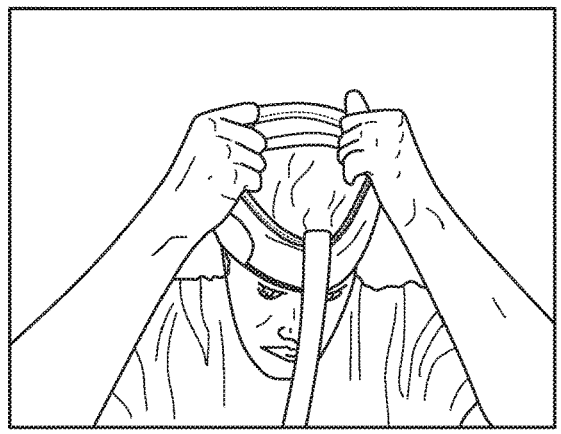
Figure 6D:
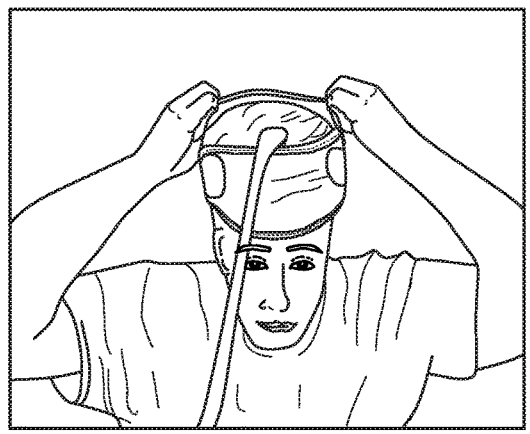
Figure 6E:
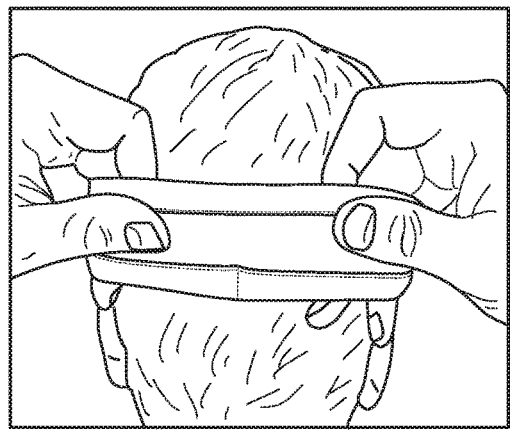
Figure 6F:
Figure 6H:
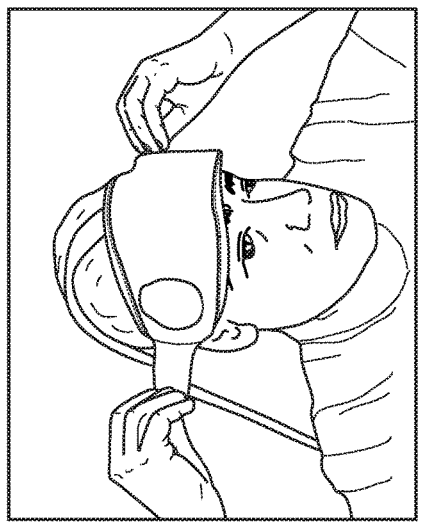
Figure 6J:
Figure 6G:
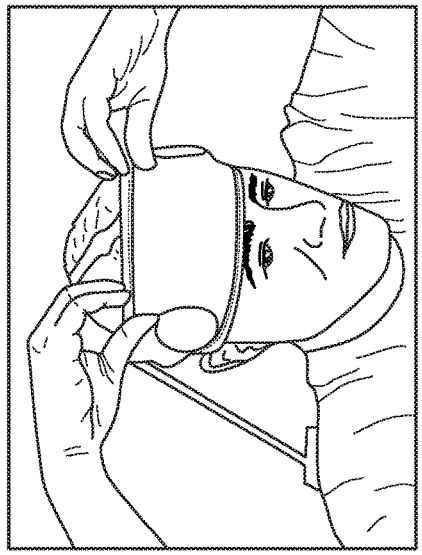
Figure 6I:

In general, the applicator may be applied to the subject's head by the subject, as illustrated in FIGS. 6A-6J. In this example, the apparatus may be powered on before placing the headgear and forehead pad on the forehead. As shown in FIG. 6A, the headgear may be held by the subject on both sides and slid over the subject's head, as shown in FIGS. 6B-6D, and over onto the forehead. The headgear may be positioned to lay flat against the back part of the subject's head right above the ear line, as shown in FIG. 6E. In some variations, the tubing connecting the applicator to the thermal regulator unit may be positioned on the middle top region of the subject's head so it lays flat against the head, as shown in FIG., 6F, and the headgear may be adjusted to fit snug against the subject's forehead and lay above the eyebrow line, as shown in FIG. 6G. FIGS. 6H and 6I shows the subject adjusting Velcro tabs on the sides of the headgear to ensure a comfortable fit against the forehead, and so that forehead pad lie flat and cover the entire forehead. Finally, the forehead pad should lie flat and cover the entire forehead, as illustrated in FIG. 6J. The thermal transfer fluid can circulate throughout the tubing into the forehead pad.

As illustrated in FIGS. 6A-6J, a thermal applicator may be held in contact with the subjects head with a head gear system. In one variation of the headgear component, a series of adjustable straps are used to selectively adjust the contact pressure of the applicator to the user. Other variations of the headgear can be constructed with and elastic type material without adjustability. The elastic nature of the material applies contact pressure to the thermal applicator. Other variations utilize both features, i.e. adjustable straps and elastic materials. In some variations the thermal applicator can be permanently integrated with the headgear and in other variations, the thermal applicator can be removable from the headgear.

In some variations it may be use useful to provide a therapeutic apparatus for enhancing a subject's sleep that is simplified, and adapted specifically for sleep treatment. For example, such as device may be configured as a thermal system for enhancing a subject's sleep, comprising: a thermal regulator unit having a housing, the thermal regulator unit configured to control the temperature of a thermal transfer fluid, a thermal applicator configured to be worn against a subject's forehead over the subject's prefrontal and frontal cortex, wherein the thermal applicator is configured to pass thermal transfer fluid from the thermal regulator unit, a controller within the thermal regulator unit configured to regulate the temperature of the thermal transfer fluid to modulate the subject's sleep by controlling a temperature of the thermal applicator; and a headgear to maintain the thermal applicator in contact with the region of the subject's head over the prefrontal and frontal cortex.

Such a simplified device may be configured to regulate the applicator temperature to a specific temperature (e.g., 30 degrees C.). Further, the applicator and/or headgear may be configured specifically to apply thermal energy to the specific location of the head (e.g., and in some variations not to apply thermal energy to other regions, e.g., by insulating other regions, including the eye orbit region, cheeks, back of the head, etc.).

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A thermal system for enhancing a subject's sleep, the system comprising:
    a thermal regulator unit having a housing, the thermal regulator unit configured to control the temperature of a thermal transfer fluid;
    a clock coupled with the thermal regulator unit;
    a display coupled with the clock and the thermal regulator unit;
    a thermal applicator configured to be worn against the subject's forehead over the subject's prefrontal and frontal cortex, wherein the thermal applicator is configured to pass thermal transfer fluid from the thermal regulator unit;
    a controller within the thermal regulator unit configured to regulate the temperature of the thermal transfer fluid based on one or more thermal control profiles to modulate the subject's sleep by controlling a temperature of the thermal applicator;
    a headgear to maintain the thermal applicator in contact with the region of the subject's head over the prefrontal and frontal cortex; and
    a cartridge containing thermal transfer fluid in a reservoir and configured to insert into a top of the thermal regulator unit, the cartridge having a valve on a bottom of the cartridge and a vent on a top of the cartridge, wherein the vent comprises a material that is air-permeable but not liquid-permeable and is configured to allow air into the reservoir.

2. The system of claim 1, further wherein the controller is configured to receive input from the clock and to modify the temperature of the thermal transfer fluid at a predetermined wakeup time to wake the subject.

3. The system of claim 1, wherein the controller is configured to maintain the temperature of the thermal transfer fluid so that the temperature of the thermal applicator is at a target temperature selected from the range consisting of: about 10 degrees C. to about 41 degrees C.

4. The system of claim 1, wherein the thermal regulator unit comprises one or more of: a Peltier device, a resistive heater, and a fan.

5. The system of claim 1, wherein the thermal applicator is adapted to thermally regulate only the region of the subject's head over the prefrontal and frontal cortex, but not other regions of the subject's head and face including the eye orbits.

6. The system of claim 1, wherein the controller comprises a plurality of thermal control profiles configured to cause the controller to regulate the temperature of the thermal transfer fluid.

7. The system of claim 1, wherein the thermal regulator unit comprises a thermal electric module configured to heat, cool, or heat and cool the thermal transfer fluid.

8. The system of claim 1, further comprising a fluid conduit connecting the thermal regulator unit and the thermal applicator, the fluid conduit configured to transfer thermal transfer fluid between the thermal regulator unit and the thermal applicator.

9. The system of claim 1, further comprising a fluid level detector within the thermal regulator unit configured to monitor the level of thermal transfer fluid within the system.

10. The system of claim 1, further comprising a control in communication with the thermal regulator unit configured to allow the subject to select the one or more thermal control profiles.

11. The system of claim 1, wherein the headgear is configured to maintain the thermal applicator in contact with just the region of the subject's head over the prefrontal and frontal cortex.

12. The system of claim 1, wherein the thermal regulator unit comprises a second reservoir for thermal transfer fluid within an internal plumbing of the thermal regulator that is configured to be thermally regulated by a thermal electric module of the thermal regulator unit, and a second valve configured to transfer fluid between the reservoir of the cartridge and the second reservoir to maintain a level of thermal transfer fluid within the second reservoir.

13. The system of claim 1, wherein the display comprises a dead front display that is visible through the housing of the thermal regulator unit when illuminated.

14. A thermal system for enhancing a subject's sleep, the system comprising:
    a thermal regulator unit having a housing, the thermal regulator unit configured to control the temperature of a thermal transfer fluid;
    a clock coupled with the thermal regulator unit;
    a display coupled with clock and the thermal regulator unit; a user input configured to allow the user to select a wakeup time;
    a thermal applicator configured to be worn against a subject's forehead over the subject's prefrontal and frontal cortex, wherein the thermal applicator is configured to pass thermal transfer fluid from the thermal regulator unit;
    a controller within the thermal regulator unit configured to regulate the temperature of the thermal transfer fluid based on one or more thermal control profiles to modulate the subject's sleep by controlling a temperature of the thermal applicator, wherein the controller is configured to modify the temperature of the thermal transfer fluid at the wakeup time;
    a headgear to maintain the thermal applicator in contact with the region of the subject's head over the prefrontal and frontal cortex; and
    a cartridge containing thermal transfer fluid in a reservoir configured to insert into a top of the thermal regulator unit, the cartridge having a valve on a bottom of the cartridge and a vent on a top of the cartridge, wherein the vent comprises a material that is air-permeable but not liquid-permeable and is configured to allow air into the reservoir.

15. The system of claim 14, wherein the thermal applicator is adapted to thermally regulate only the region of the subject's head over the prefrontal and frontal cortex, but not other regions of the subject's head and face including the eye orbits.

16. The system of claim 14, wherein the controller comprises a plurality of thermal control profiles configured to cause the controller to regulate the temperature of the thermal transfer fluid.

17. The system of claim 14, wherein the thermal regulator unit comprises a thermal electric module configured to heat, cool, or heat and cool the thermal transfer fluid.

18. The system of claim 14, further comprising an insulated fluid conduit connecting the thermal regulator unit and the thermal applicator, the fluid conduit configured to transfer thermal transfer fluid between the thermal regulator unit and the thermal applicator.

19. The system of claim 14, further comprising a fluid level detector within the thermal regulator unit configured to monitor the level of thermal transfer fluid within the system.

20. The system of claim 14, further comprising a control in communication with the thermal regulator unit configured to allow the subject to select the one or more thermal control profiles.

21. The system of claim 14, wherein the headgear is configured to maintain the thermal applicator in contact with just the region of the subject's head over the prefrontal and frontal cortex.

22. The system of claim 14, wherein the thermal regulator unit comprises a second reservoir for thermal transfer fluid within an internal plumbing of the thermal regulator that is configured to be thermally regulated by a thermal electric module of the thermal regulator unit, and a second valve configured to transfer fluid between the reservoir of the cartridge and the second reservoir to maintain a level of thermal transfer fluid within the second reservoir.

23. The system of claim 14, wherein the thermal regulator unit comprises one or more of: a Peltier device, a resistive heater, and a fan.

24. A thermal system for enhancing a subject's sleep, the system comprising:
a thermal regulator unit having a housing, the thermal regulator unit configured to control the temperature of a thermal transfer fluid;
a thermal electric module within the thermal regulator unit configured to heat, cool, or heat and cool the thermal transfer fluid;
a first reservoir of thermal transfer fluid within an internal plumbing of the thermal regulator, wherein the first reservoir is configured to be thermally regulated by the thermal electric module;
a second reservoir of thermal transfer fluid that is not thermally regulated by the thermal electric module, wherein the second reservoir comprises a removable cartridge configured to insert into a top of the thermal regulator unit, the cartridge having a first valve on a bottom of the cartridge and a vent on a top of the cartridge, wherein the vent comprises a material that is air-permeable but not liquid-permeable and is configured to allow air into the second reservoir;
a second valve configured to transfer fluid between the first reservoir and the second reservoir to maintain a level of thermal transfer fluid within the first reservoir;
a thermal applicator configured to be worn against a subject's forehead over the subject's prefrontal and frontal cortex, wherein the thermal applicator is configured to pass thermal transfer fluid from the thermal regulator unit;
a controller within the thermal regulator unit configured to regulate the temperature of the thermal transfer fluid based on one or more thermal control profiles to modulate the subject's sleep by controlling a temperature of the thermal applicator, wherein the controller is configured to modify the temperature of the thermal transfer fluid at the wakeup time to wake the subject; and
a headgear to maintain the thermal applicator in contact with the region of the subject's head over the prefrontal and frontal cortex.

25. The system of claim 24, wherein the controller is configured to maintain the temperature of the thermal transfer fluid in the first reservoir so that the temperature of the thermal applicator is at a target temperature selected from the range consisting of: about 10 degrees C. to about 41 degrees C.

26. The system of claim 24, further wherein the controller is configured to modify the temperature of the thermal transfer fluid at a predetermined wakeup time.

27. The system of claim 24, further comprising a clock having a clock display.

28. The system of claim 24, wherein the thermal applicator is adapted to thermally regulate only the region of the subject's head over the prefrontal and frontal cortex, but not other regions of the subject's head and face including the eye orbits.

29. The system of claim 24, wherein the controller comprises a plurality of thermal control profiles configured to cause the controller to regulate the temperature of the thermal transfer fluid.

30. The system of claim 24, wherein the thermal regulator unit comprises one or more of: a Peltier device, a resistive heater, and a fan.

31. The system of claim 24, further comprising a fluid conduit connecting the thermal regulator unit and the thermal applicator, the fluid conduit configured to transfer thermal transfer fluid between the first reservoir and the thermal applicator.

32. The system of claim 24, further comprising a fluid level detector within the first reservoir configured to monitor the level of thermal transfer fluid within the first reservoir.

33. The system of claim 24, further comprising a control in communication with the thermal regulator unit configured to allow the subject to select the one or more thermal control profiles.

34. The system of claim 24, wherein the headgear is configured to maintain the thermal applicator in contact with just the region of the subject's head over the prefrontal and frontal cortex.

* * * * *

UNITED STATES PATENT AND TRADEMARK OFFICE
CERTIFICATE OF CORRECTION

PATENT NO. : 10,058,674 B2
APPLICATION NO. : 14/758438
DATED : August 28, 2018
INVENTOR(S) : Rick W. Walker et al.

It is certified that error appears in the above-identified patent and that said Letters Patent is hereby corrected as shown below:

In the Claims

Claim 24, Column 18, Line 14; after "transfer fluid at" and before "wakeup time", delete "the" and add --a--.

Signed and Sealed this
Seventeenth Day of September, 2019

Andrei Iancu
*Director of the United States Patent and Trademark Office*